US007906505B2

(12) United States Patent
Bruncko et al.

(10) Patent No.: US 7,906,505 B2
(45) Date of Patent: *Mar. 15, 2011

(54) APOPTOSIS PROMOTERS

(75) Inventors: Milan Bruncko, Green Oaks, IL (US); Hong Ding, Gurnee, IL (US); Steven W. Elmore, Northbrook, IL (US); Aaron R. Kunzer, Schaumburg, IL (US); Christopher L. Lynch, Trevor, WI (US); William J. McClellan, Waukegan, IL (US); Cheol Min Park, Gurnee, IL (US); Xiahong Song, Grayslake, IL (US); Xilu Wang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/772,951

(22) Filed: May 3, 2010

(65) Prior Publication Data
US 2010/0249133 A1 Sep. 30, 2010

Related U.S. Application Data

(63) Continuation of application No. 12/120,914, filed on May 15, 2008, now Pat. No. 7,709,467, which is a continuation of application No. 11/432,937, filed on May 12, 2006, now Pat. No. 7,390,799.

(60) Provisional application No. 60/718,618, filed on Sep. 20, 2005, provisional application No. 60/680,107, filed on May 12, 2005.

(51) Int. Cl.
C07D 413/02 (2006.01)
C07D 403/02 (2006.01)
A61K 31/553 (2006.01)
A61K 31/55 (2006.01)
A61K 31/5377 (2006.01)

(52) U.S. Cl. ........... 514/211.15; 514/217.05; 514/235.5; 514/253.04; 514/254.01

(58) Field of Classification Search .............. 514/211.15, 514/217.05, 235.5, 253.04, 254.01
See application file for complete search history.

(56) References Cited

U.S. PATENT DOCUMENTS

| 2,413,833 | A | * | 1/1947 | Kyrides |
|---|---|---|---|---|
| 5,138,069 | A | | 8/1992 | Carini et al. |
| 6,410,584 | B1 | | 6/2002 | Pamukcu et al. |
| 6,720,338 | B2 | * | 4/2004 | Augeri et al. |
| 7,030,115 | B2 | | 4/2006 | Elmore et al. |
| 7,358,251 | B2 | | 4/2008 | Elmore et al. |
| 7,390,799 | B2 | * | 6/2008 | Bruncko et al. ......... 514/211.15 |
| 7,449,485 | B2 | | 11/2008 | Elmore et al. |
| 7,504,512 | B2 | | 3/2009 | Augeri et al. |
| 7,585,858 | B2 | | 9/2009 | Elmore et al. |
| 7,642,260 | B2 | | 1/2010 | Bruncko et al. |
| 7,709,467 | B2 | | 5/2010 | Bruncko et al. |
| 7,767,684 | B2 | * | 8/2010 | Bruncko et al. |
| 2003/0119894 | A1 | | 6/2003 | Murthy et al. |
| 2003/0236247 | A1 | * | 12/2003 | Elmore et al. |
| 2005/0159427 | A1 | | 7/2005 | Bruncko et al. |
| 2006/0128706 | A1 | | 7/2006 | Bruncko et al. |
| 2006/0258657 | A1 | * | 11/2006 | Bruncko et al. |
| 2007/0072860 | A1 | | 3/2007 | Bruncko et al. |
| 2008/0076779 | A1 | | 3/2008 | Elmore et al. |

FOREIGN PATENT DOCUMENTS

| EP | 1685119 | | 11/2004 |
|---|---|---|---|
| EP | 1685119 A1 | * | 8/2006 |
| NZ | 230136 | | 12/1991 |
| TW | 200526559 | | 11/2004 |
| TW | 200526559 | * | 8/2005 |
| WO | WO 02/24636 | | 3/2002 |
| WO | WO 02/098848 | | 12/2002 |
| WO | WO02098848 A1 | * | 12/2002 |
| WO | WO 03/040107 | | 5/2003 |
| WO | WO 03/080586 | | 10/2003 |
| WO | WO 2004/043950 | | 5/2004 |
| WO | WO 2004/048329 | | 6/2004 |
| WO | WO 2005/049593 | | 6/2005 |
| WO | WO 2005/049594 | | 6/2005 |
| WO | WO2005049593 A2 | * | 6/2005 |
| WO | WO2005049594 A1 | * | 6/2005 |
| WO | WO 2008/017121 | | 2/2008 |
| WO | WO 2008/017123 | | 2/2008 |
| WO | WO2008017121 A1 | * | 2/2008 |
| WO | WO2008017123 A1 | | 2/2008 |

OTHER PUBLICATIONS

Amundson et al, "An Informatics Approach Identifying Markers of Chemosensitivity in Human Cancer Cell Lines," Cancer Research, 60, 6101-6110 (2000).
Applicant's Amendment and Response dated Nov. 2, 2009, pp. 1-29, in response to U.S.P.T.O. Office Action for U.S. Appl. No. 11/127,940.
Applicant's Amendment and Response dated Nov. 19, 2009, pp. 1-6 in response to U.S.P.T.O. Office Action for U.S. Appl. No. 11/491,851.
Applicant's Amendment and Response dated Oct. 8, 2009, pp. 1-7, in response to U.S.P.T.O. Restriction Requirement for U.S. Appl. No. 11/600,445.
Banker, Gilbert S. et al., Modern Pharmaceuticals, 1996, Marcel Dekker, New York, pp. 596 and 451.
Cheng et al, "Synthesis of N-Heteroaryl-7-azabicyclo[2.2.1]heptane Derivatives via Palladium-Bisimidazol-2-ylidene Complex Catalyzed Amination Reactions," Organic Letters, 3(9), 1371-1374 (2001).
Corbett et al., "Discovery and preclinical antitumor efficacy evaluations of LY32262 and LY33169," Investigational New Drugs, 2003, vol. 21:33-45.
Degterev, et al., "Identification of small-molecule inhibitors of interaction between the BH3 domain and Bcl-$x_L$," Nature Cell Biology, 2001, vol. 3, pp. 173-182.

(Continued)

Primary Examiner — Kahsay T Habte
(74) Attorney, Agent, or Firm — Jones Day

(57) ABSTRACT

Compounds which inhibit the activity of anti-apoptotic family protein members, compositions containing the compounds and methods of treating diseases during which occur expression one or more than one of an anti-apoptotic family protein member are disclosed.

4 Claims, 7 Drawing Sheets

OTHER PUBLICATIONS

Enyedy, et al., "Discovery of Small-Molecule Inhibitors of Bcl-2 through Structure-Based Computer Screening," J. Med. Chem., 2001, 44, pp. 4313-4324.

Gambacorta, et al, "Bicyclo[3.3.1]nonane Approach to Triquinanes. Formal Synthesis of (+/−)Δ9(12)Campnellene and (+/−) Δ9(12)Capnellene-8β-10α-diol," Tetrahedron, 48(21), 4459-4464 (1992).

Holzelova, et al., "Autoimmune Lymphoproliferative Syndrome with Somatic Fas Mutations", NEJM, 351, 1409-1418 (2004).

ISA, PCT International Preliminary Report on Patentability dated May 15, 2006, in International Application No. PCT/US2004/036770, filed Nov. 3, 2004.

ISA, PCT International Preliminary Report on Patentability dated May 15, 2006, in International Application No. PCT/US2004/037911, filed Nov. 12, 2004.

ISA, PCT International Search Report dated May 13, 2005, in International Application No. PCT/US2004/036770, filed Nov. 3, 2004.

ISA, PCT International Search Report dated May 13, 2005, in International Application No. PCT/US2004/037911, filed Nov. 12, 2004.

ISA, PCT International Search Report dated Mar. 22, 2007 for International Application No. PCT/US2006/018799.

ISA, Written Opinion for International Application No. PCT/US2006/018799, dated Mar. 22, 2007.

Oltersdorf, et al., "An inhibitor of Bcl-2 Family proteins induces regression of solid tumours", Nature, 2005, 4 35, 677-681.

Petros, et al., "Solution structure of the antiapoptotic protein bcl-2", PNAS, 98, 3012-3017.

Puck, et al., "Immune Disorders Caused by Defects in the Caspase Cascade", Current Allergy and Asthma Reports, 3, 378-384 (2003).

Rengan, et al-, "Actin cytoskeletal function is spared, but apoptosis is increased, in WAS patient Hematopoietic cells", Blood, 95(4), 1283-1292 (2000).

Sattler, et al., "Structure of Bcl-xL-Bak Peptide Complex: Recognition Between Regulators of Apoptosis", Science, 275, 983-986 (1997).

Shimazaki, et al., "Evaluation of apoptosis as a prognostic factor in myelodysplastic syndromes", British J Haematology, 110(3), 584-590 (2000).

Tse et al., "ABT-263: A Potent and Orally Bioavailable Bcl-2 Family Inhibitor," Cancer Research May 1, 2008, 68(9):3421-3428.

U.S.P.T.O., Office Action/Restriction Requirement dated Apr. 25, 2008, cover sheet and pp. 1-7, for U.S. Appl. No. 11/127,940.

U.S.P.T.O. Non-Final Office Action dated Sep. 12, 2008 in U.S. Appl. No. 11/202,827.

U.S.P.T.O., Non-final Office Action dated Nov. 28, 2008 in U.S. Appl. No. 12/120,914.

U.S.P.T.O., Notice of Allowance and Fee(s) Due, dated Jul. 1, 2009, p. 1, for U.S. Appl. No. 11/202,827.

U.S.P.T.O., Notice of Allowability, dated Jul. 1, 2009, p. 1-2, for U.S. Appl. No. 11/202,827.

U.S.P.T.O., Interview Summary, dated Jul. 1, 2009, p. 1, for U.S. Appl. No. 11/202,827.

U.S.P.T.O., Examiner's Amendment, dated Jul. 1, 2009, pp. 2-4, for U.S. Appl. No. 11/202,827.

U.S.P.T.O., Final Office Action dated Aug. 12, 2009 in U.S. Appl. No. 12/120,914.

Wang, et al., "Structure-based discovery of an organic compound that binds Bcl-2 protein and induces apoptosis of tumor cells," PNAS, Jun. 20, 2000, vol. 97, No. 13, pp. 7124-7129.

Wang, et al., "A novel small molecule inhibitor of Bcl-$X_L$ inhibits tumor growth in a human head and neck squamous cell carcinoma xenograft model," Proceedings of the American Association for Cancer Research, Jul. 2003, vol. 44, $2^{nd}$ Ed., p. 942, #4740 Abstract.

Wang, et al., "An Efficient Synthesis of ABT-263, a Novel Inhibition of Anti-apoptotic Bcl-2 Proteins," Synthesis, 2008, 15, 2398-2404.

Wolff, Manfred E., Burger's Medicinal Chemistry and Drug Discovery, Fifth Ed. vol. 1: Principles and Practice, John Wiley & Sons, 1995, pp. 975-977.

Zhang, et al., "Development of a high-throughput fluorescence polarization assay for Bcl-xL", Analytical Biochemistry, 307, 70-75 (2002).

Amundson et al., "An Informatics Approach Identifying Markers of Chemosensitivity in Human Cancer Cell Lines," Cancer Research, 2000, 60, pp. 6101-6110.

Applicant's Amendment and Response dated Nov. 19, 2009, pp. 1-6 in response to U.S.P.T.O. Office Action for U.S. Appl. No. 11/491,851.

Applicant's Amendment and Response dated Nov. 2, 2009, pp. 1-29, in response to U.S.P.T.O. Office Action for U.S. Appl. No. 11/127,940.

Applicant's Amendment and Response dated Oct. 8, 2009, pp. 1-7, in response to U.S.P.T.O. Restriction Requirement for U.S. Appl. No. 11/600,445.

Cheng, et al., "Synthesis of N-Heteroaryl-7-azabicyclo[2.2.1]heptane Derivatives via Palladium-Bisimidazol-2-ylidene Complex Catalyzed Amination Reactions," Organic Letters, 2001, 3—Issue 9, pp. 1371-1374.

Gambacorta et al., "Bicyclo[3.3.1]nonane Approach to Triquinanes. Formal Synthesis of (+/−)9(12)Campnellene and (+/−)(+/−−)delta 9(12)Capnellene-8β-10a-diol", Tetrahedron 1992, 48 Issue 21, pp. 4459-4464.

Holzelova et al., "Autoimmune Lymphoproliferative Syndrome with Somatic Fas Mutations," New England Journal of Medicine, 2004, 351, pp. 1409-1418.

International Search Report for application No. PCT/US2006/018799, Mailed on Mar. 22, 2007, 3 pages.

ISA/EPO, Written Opinion for International Application No. PCT/US2006/018799, dated Mar. 22, 2007.

Oltersdorf et al., "An inhibitor of Bcl-2 family proteins induces regression of solid tumours," Nature, 2005, 435.

Petros et al., Solution structure of the antiapoptotic protein bcl-2, PNAS, 2001, 98 (6), 3012-3017.

Puck,et al., "Immune Disorders Caused by Defects in the Caspase Cascade," Current Allergy and Asthma Reports, 2003, 3, pp. 378-384.

Rengan. et al., "Actin cytoskeletal function is spared, but apoptosis is increased, in WAS patient hematopoietic cells," Blood, 2000, 95-Issue 4, pp. 1283-1292.

Sattler M. et al., Structure of Bcl-xL-Bak Peptide Complex: Recognition Between Regulators of Apoptosis, Science, 1997, 275, 983-986.

Shimazaki et al., "Evaluation of apoptosis as a prognostic factor in myelodysplastic syndromes", British J Haematology, 2000, 110 Issue 3, pp. 584-590.

Tse et al., "ABT-263: A Potent and Orally Bioavailable Bcl-2 Family Inhibitor," CancerResearch , 2008, 68—Issue9, pp. 3421-3428.

U.S.P.T.O., Examiners Amendment, dated Jul. 1, 2009, pp. 2-4, for U.S. Appl. No. 11/202,827.

U.S.P.T.O., Interview Summary, dated Jul. 1, 2009, p. 1, for U.S. Appl. No. 11/202,827.

U.S.P.T.O. Non-Final Office Action dated Sep. 12, 2008, in U.S. Appl. No. 11/202,827, filed Aug. 12, 2005.

U.S.P.T.O., Notice of Allowability, dated Jul. 1, 2009, p. 1-2, for U.S. Appl. No. 11/202,827.

U.S.P.T.O., Notice of Allowance and Fee(s) Due, dated Jul. 1, 2009, p. 1, for U.S. Appl. No. 11/202,827.

U.S.P.T.O., Office Action/Restriction Requirement dated Apr. 25, 2008, cover sheet and pp. 1-7, for U.S. Appl. No. 11/127,940.

Zhang et al., "Development of a high-throughput fluorescence polarization assay for Bcl-Xl," Analytical Biochemistry , 2002, 307, pp. 70-75.

* cited by examiner

APOPTOSIS PROMOTERS

CROSS REFERENCE SECTION

This application is a continuation of U.S. application Ser. No. 12/120,914, filed May 15, 2008 now U.S. Pat. No. 7,709,467, which is a continuation of U.S. patent application Ser. No. 11/432,937, filed May 12, 2006, now U.S. Pat. No. 7,390,799, which claims priority to U.S. Provisional Application No. 60/718,618, filed Sep. 20, 2005 and U.S. Application No. 60/680,107, filed May 12, 2005.

FIELD OF THE INVENTION

This invention comprises compounds which inhibit the activity of anti-apoptotic Bcl-2 family protein members, compositions containing the compounds and methods of treating diseases during which are expressed one or more than one of an anti-apoptotic family protein member.

BACKGROUND OF THE INVENTION

Anti-apoptotic Bcl-2 family protein members are associated with a number of diseases and thus are under investigation as potential therapeutic drug targets. These important targets for interventional therapy include, for example, the Bcl-2 family of proteins Bcl-2, Bcl-$X_L$ and Bcl-w. Recently inhibitors of Bcl-2 family members have been reported in the literature, see, for example, WO 2005/049594, Oltersdorf, et. al. Nature 2005, 435, 677-681, U.S. Pat. No. 6,720,338 and U.S. Pat. No. 7,030,115. While this art teaches inhibitors having high binding to the target protein, this is only one of many parameters that must be considered as a compound is investigated for further or continued drug development. As part of this development, it is highly desirable to produce compounds that are efficacious in animal models of cancer after oral administration. To achieve this oral efficacy, it is well known in the art that a compound must not only display potent activity against a tumor type or cell line under investigation, but must also achieve acceptable levels of systemic exposure after oral administration. A typical measure of cellular activity is the concentration eliciting 50% cellular effect ($EC_{50}$). A typical measure of systemic exposure is the area under the curve resulting from graphing the plasma compound concentration after oral administration vs. time (AUC). The ratio between these parameters (AUC/$EC_{50}$) is well known in the art to constitute a useful pharmacodynamic parameter to predict oral efficacy.

The inventors have discovered that while compounds taught in the art may have either potent cellular efficacies or high systemic exposures after oral administration to animals, they do not possess both properties. This results in a low AUC/$EC_{50}$ ratio and renders these compounds not orally efficacious. This invention is directed to a series of haloalkylsulonylaryl analogs that demonstrate enhanced and unexpected properties with respect to cellular efficacy and systemic exposure after oral administration in animals. Specifically, compounds of this invention maintain potent cellular efficacy while exhibiting suitable systemic exposure after oral administration to animals. This results in AUC/$EC_{50}$ ratios significantly higher than that of the compounds taught in the art.

SUMMARY OF THE INVENTION

Figure 1:
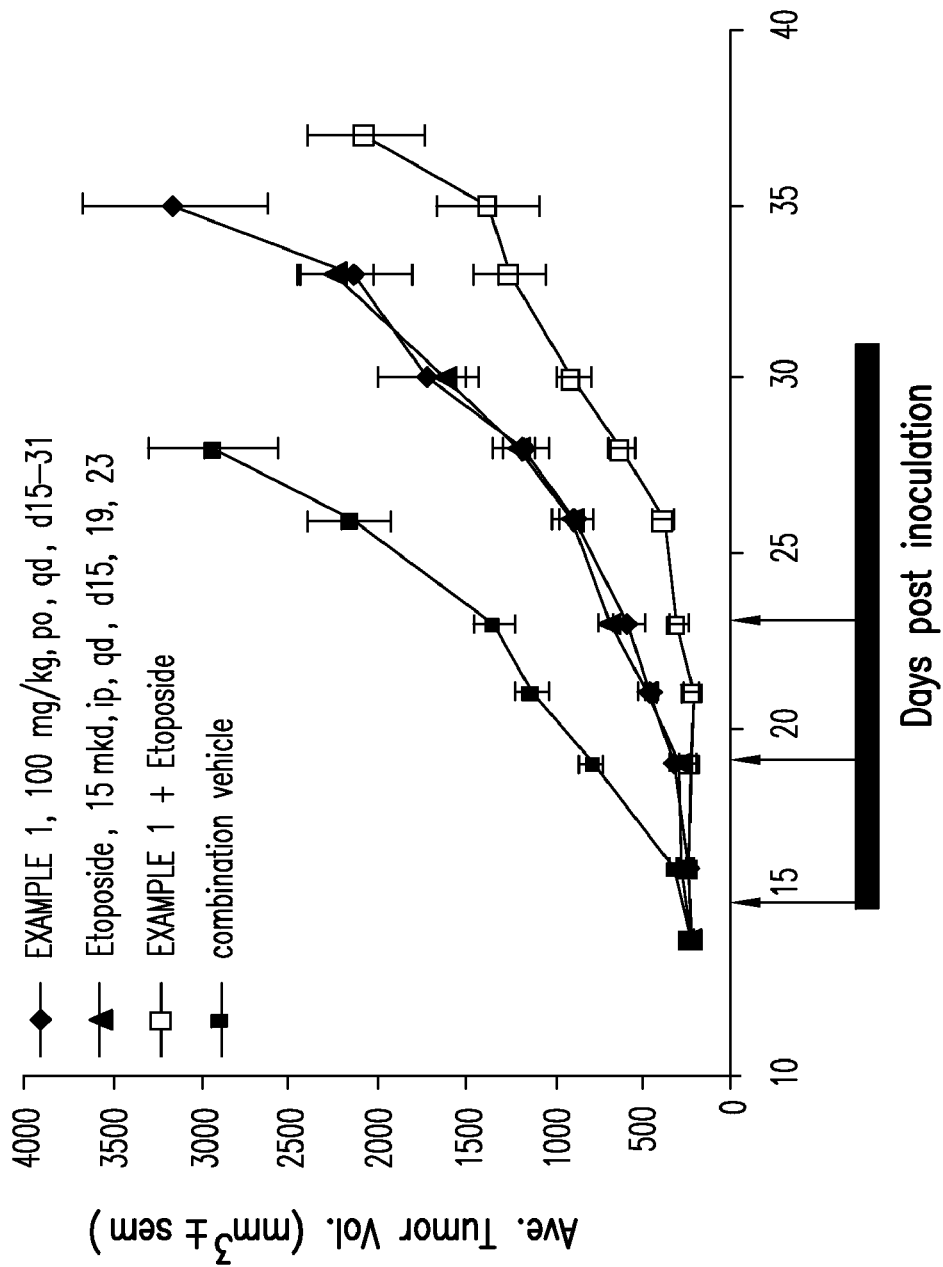
FIG. 1 shows comparitive antitumorgenesis of EXAMPLE 1, etoposide and combinations thereof on B-cell lymphoma.

One embodiment of this invention comprises compounds having formula (II)

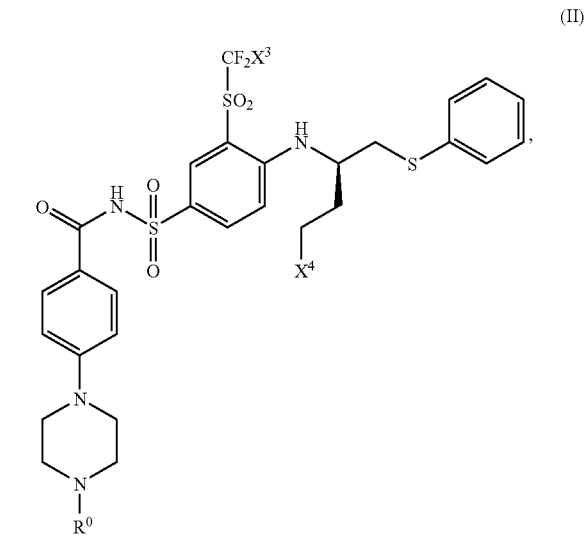

(II)

and therapeutically acceptable salts, prodrugs, salts of prodrugs and metabolites thereof, wherein $X^3$ is Cl or F;

$X^4$ is azepan-1-yl, morpholin-1-yl, 1,4-oxazepan-4-yl, pyrrolidin-1-yl, N(CH$_3$)$_2$, N(CH$_3$)(CH(CH$_3$)$_2$), 7-azabicyclo[2.2.1]heptan-1-yl or 2-oxa-5-azabicyclo[2.2.1]hept-5-yl, and $R^0$ is

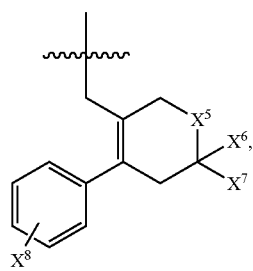

wherein
$X^5$ is CH$_2$, C(CH$_3$)$_2$ or CH$_2$CH$_2$;
$X^6$ and $X^7$ are both hydrogen or are both methyl; and
$X^8$ is F, Cl, Br or I; or X⁴ is azepan-1-yl, morpholin-1-yl, pyrrolidin-1-yl, N(CH₃)(CH(CH₃)₂) or 7-azabicyclo[2.2.1]heptan-1-yl, and R⁰ is

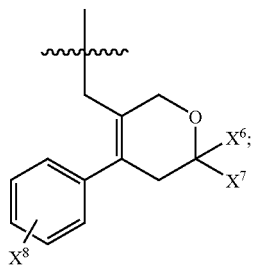

or

X⁴ is N(CH₃)₂ or morpholin-1-yl, and R⁰ is

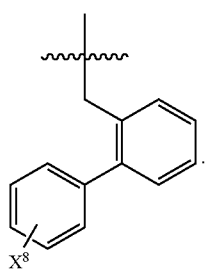

Another embodiment comprises compounds having formula (II), and therapeutically acceptable salts, prodrugs, salts of prodrugs and metabolites thereof, wherein X³ is Cl or F;

X⁴ is azepan-1-yl, morpholin-1-yl, 1,4-oxazepan-4-yl, pyrrolidin-1-yl, N(CH₃)₂, N(CH₃)(CH(CH₃)₂), 7-azabicyclo[2.2.1]heptan-1-yl or 2-oxa-5-azabicyclo[2.2.1]hept-5-yl, and R⁰ is

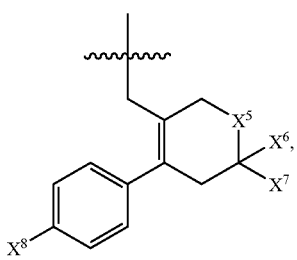

wherein
X⁵ is CH₂, C(CH₃)₂ or CH₂CH₂;
X⁶ and X⁷ are both hydrogen or are both methyl; and
X⁸ is F, Cl, Br or I; or X⁴ is azepan-1-yl, morpholin-1-yl, pyrrolidin-1-yl, N(CH₃)(CH(CH₃)₂) or 7-azabicyclo[2.2.1]heptan-1-yl, and R⁰ is

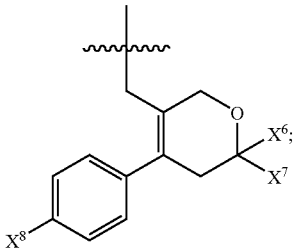

or

X⁴ is N(CH₃)₂ or morpholin-1-yl, and R⁰ is

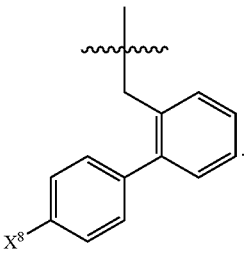

Still another embodiment comprises compounds having formula (II), and therapeutically acceptable salts, prodrugs, salts of prodrugs and metabolites thereof, wherein X³ is Cl or F;

X⁴ is azepan-1-yl, morpholin-1-yl, 1,4-oxazepan-4-yl, pyrrolidin-1-yl, N(CH₃)₂, N(CH₃)(CH(CH₃)₂), 7-azabicyclo[2.2.1]heptan-1-yl or 2-oxa-5-azabicyclo[2.2.1]hept-5-yl, and R⁰ is

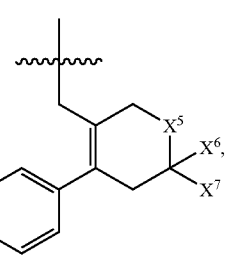

wherein X⁵ is CH₂, C(CH₃)₂ or CH₂CH₂, and X⁶ and X⁷ are both hydrogen or are both methyl; and
X⁸ is F, Cl, Br or I.

Still another embodiment comprises compounds having formula (II), and therapeutically acceptable salts, prodrugs, salts of prodrugs and metabolites thereof, wherein X³ is Cl or F;

$X^4$ is azepan-1-yl, morpholin-1-yl, pyrrolidin-1-yl, $N(CH_3)(CH(CH_3)_2)$ or 7-azabicyclo[2.2.1]heptan-1-yl;
$R^0$ is

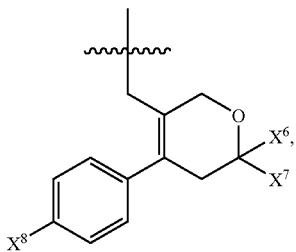

wherein $X^6$ and $X^7$ are both hydrogen or are both methyl; and $X^8$ is F, Cl, Br or I.

Still another embodiment comprises compounds having formula (II), and therapeutically acceptable salts, prodrugs, salts of prodrugs and metabolites thereof, wherein $X^3$ is Cl or F;
$X^4$ is $N(CH_3)_2$ or morpholin-1-yl;
$R^0$ is

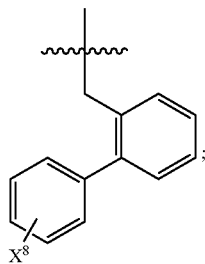

and
$X^8$ is F, Cl, Br or I.

Still another embodiment comprises a compound having formula (II), and therapeutically acceptable salts, prodrugs, salts of prodrugs and metabolites thereof, wherein $X^3$ is F; $X^4$ is morpholin-1-yl;
$R^0$ is

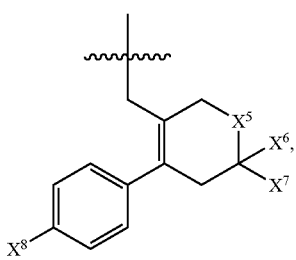

wherein $X^5$ is $C(CH_3)_2$; $X^6$ and $X^7$ are both methyl; and $X^8$ is Cl.

Still another embodiment comprises
N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide,
3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide,
3-((chloro(difluoro)methyl)sulfonyl)-N-(4-(4-((2-(4-chlorophenyl)-1-cyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide,
N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide,
N-(4-(4-((2-(4-chlorophenyl)-1-cyclohepten-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide,
3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide,
N-(4-(4-((2-(4-chlorophenyl)cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide,
4-(((1R)-3-(7-azabicyclo[2.2.1]hept-7-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide,
N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide,
N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide,
3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide,
N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide,
3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide,
N-(4-(4-((2-(4-chlorophenyl)-4,4-d methylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide,
N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide,
4-(((1R)-3-(azepan-1-yl)-1-((phenylsulfanyl)methyl)propyl)amino)-N-(4-(4-((2-(4-chlorophenyl)-1-cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohept-1-en-1-yl)methyl) piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethyl-1-cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino) benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino) benzenesulfonamide.

N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohex-1-en-1-yl)methyl) piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl) piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide.

3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)cyclohex-1-en-1-yl)methyl) piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)-3-((trifluoromethyl)sulfonyl) benzenesulfonamide N-(4-(4-((4'-chloro(1,1'-biphenyl)-2-yl)methyl)-1-piperazinyl)benzoyl)-4-(((1R)-3-(dimethylamino)-1-((phenylsulfanyl)methyl)propyl)amino)-3-((trifluoromethyl)sulfonyl)benzenesulfonamide and N-(4-(4-((4'-chloro(1,1'-biphenyl)-2-yl)methyl)-1-piperazinyl)benzoyl)-4-(((1R)-3-(4-morpholinyl)-1-((phenylsulfanyl)methyl)propyl)amino)-3-((trifluoromethyl)sulfonyl)benzenesulfonamide, and therapeutically acceptable salts, prodrugs, salts of prodrugs and metabolites thereof.

Still another embodiment comprises compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (II).

Still another embodiment comprises methods of treating diseases in a patient during which are expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (II).

Still another embodiment comprises compositions comprising an excipient and a therapeutically effective amount of the compound having formula (II) for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof.

Still another embodiment comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto a therapeutically effective amount of a compound having formula (II).

Still another embodiment comprises compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer, said compositions comprising an excipient and a therapeutically effective amount of the compound having formula (II).

Still another embodiment comprises methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer in a patient, said methods comprising administering to the patient a therapeutically effective amount of a compound having formula (II).

Still another embodiment comprises compositions for treating diseases in a patient during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (II) a therapeutically effective amount of one additional therapeutic agent or more than one additional therapeutic agent.

Still another embodiment comprises methods of treating diseases in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (II) and a therapeutically effective amount of one additional therapeutic agent or more than one additional therapeutic agent.

Still another embodiment comprises compositions for treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers, said compositions comprising an excipient and therapeutically effective amount of a compound having formula (II) and one additional therapeutic agent or more than one additional therapeutic agent.

Still another embodiment comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto therapeutically effective amounts of a compound having formula (II) and one additional therapeutic agent or more than one additional therapeutic agent.

Still another embodiment comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto therapeutically effective amounts of a compound having formula (II) and one or more than one of etoposide vincristine CHOP, rituximab, rapamycin, R-CHOP or bortezomib.

Still another embodiment comprises methods of treating B-cell lymphoma in a patient comprising administering thereto a therapeutically acceptable amounts of a compound having formula (II) and etoposide.

Still another embodiment comprises methods of treating B-cell lymphoma in a patient comprising administering thereto therapeutically acceptable amounts of a compound having formula (II) and vincristine.

Still another embodiment comprises methods of treating B-cell lymphoma in a patient comprising administering thereto therapeutically acceptable amounts of a compound having formula (II) and CHOP.

Still another embodiment comprises methods of treating B-cell lymphoma in a patient comprising administering thereto therapeutically acceptable amounts of a compound having formula (II) and rituximab.

Still another embodiment comprises methods of treating B-cell lymphoma in a patient comprising administering thereto therapeutically acceptable amounts of a compound having formula (II) and rapamycin.

Still another embodiment comprises methods of treating mantle cell lymphoma in a patient comprising administering thereto therapeutically acceptable amounts of a compound having formula (II) and R-CHOP.

Still another embodiment comprises methods of treating mantle cell lymphoma in a patient comprising administering thereto therapeutically acceptable amounts of a compound having formula (II) and bortezomib.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof and that monovalent moieties having more than one atom are attached through their left ends.

It is also meant to be understood that a specific embodiment of a variable moiety may be the same or different as another specific embodiment having the same identifier.

The term "antitumorigenesis," as used herein, means reduction of tumor growth.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds having formula (II) having NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (II), produced by in vitro or in vivo metabolic processes, may also have utility for treating diseases associated with expression of an anti-apoptotic family protein member such as of BCl-$X_L$ protein, Bcl-2 protein or Bcl-w protein.

Compounds having formula (II) may also be radiolabeled with a radioactive isotope such as a radioactive isotope of carbon (i.e. $^{13}C$), hydrogen (i.e. $^{3}H$), nitrogen (i.e. $^{15}N$), phosphorus (i.e. $^{32}P$), sulfur (i.e. $^{35}S$) or iodide (i.e. $^{125}I$). Radioactive isotopes may be incorporated into the compounds having formula (II) by reacting the same and a radioactive derivitizing agent or by incorporating a radiolabeled intermediate into their syntheses. The radiolabeled compounds of formula (II) are useful for both prognostic and diagnostic applications as well as for in vivo and in vitro imaging.

Certain precursor compounds which may be metabolized in vitro or in vivo to form compounds having formula (II) may also have utility for treating diseases associated with expression of an anti-apoptotic family protein member such as of BCl-$X_L$ protein, Bcl-2 protein or Bcl-w protein.

Compounds having formula (II) may exist as acid addition salts, basic addition salts or zwitterions. Salts of compounds having formula (II) are prepared during their isolation or following their purification. Acid addition salts are those derived from the reaction of a compound having formula (II) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (II) are meant to be embraced by this invention. Basic addition salts of compounds are those derived from the reaction of the compounds having formula (II) with the bicarbonate, carbonate, hydroxide or phosphate of cations such as lithium, sodium, potassium, calcium and magnesium.

Compounds having formula (II) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature by means of, for example, a stent.

Therapeutically effective amounts of a compound having formula (II) depend on recipient of treatment, disease treated and severity thereof, composition comprising it, time of administration, route of administration, duration of treatment, potency, rate of clearance and whether or not another drug is co-administered. The amount of a compound having formula (II) used to make a composition to be administered daily to a patient in a single dose or in divided doses is from about 0.03 to about 200 mg/kg body weight. Single dose compositions contain these amounts or a combination of sub-multiples thereof.

Compounds having formula (II) may be administered with or without an excipient. Excipients include, but are not limited to, encapsulators and additives such as absorption accelerators, antioxidants, hinders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (II) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (II) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (II) to be administered osmotically include, but are not limited to, chlorofluorohydrocarbons, ethanol, water, mixtures thereof and the like. Excipients for preparation of compositions comprising a compound having formula (II) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (II) to be administered rectally or vaginally include, but are not limited to, cocoa butter, polyethylene glycol, wax, mixtures thereof and the like.

This invention also comprises combination therapeutic methods of treating disease conditions involving abnormal cell growth and/or dysregulated apoptosis, such as cancer, in a patient comprising administering thereto a therapeutically effective amount of a pharmaceutical composition comprising a compound having formula (II) and a therapeutically effective amount of one or more than one additional therapeutic agents and/or ionizing radiation.

The combination therapeutic methods include administering compositions of a compound having formula (II) and one or more than one additional therapeutic agents or ionizing radiation to a patient using any desired dosing and/or scheduling regimen.

Compounds having formula (II) may be administered with one or more than one additional therapeutic agents, wherein the additional therapeutic agents include ionizing radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adriamycine® (hydroxydoxorubicin); O: Vincristine (Oncovin®); P: prednisone). paclitaxel, rapamycin, Rituxin® (rituximab), vincristine and the like.

Compounds having formula (II) are also expected to be useful as chemotherapeutic agents in combination with therapeutic agents that include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs.

MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, Iressa (gefitinib), Tarceva (erlotinib or OSI-774), Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596:

Examples of VEGFR inhibitors include, but are not limited to, Avastin (bevacizumab), Sutent (sunitinib, SU11248), Nexavar (sorafenib, BAY43-9006). CP-547,632, axitinib (AG13736), Zactima (vandetanib, ZD-6474), AEE788, AZD-2171, VEGF trap, Vatalanib (PTK-787, ZK-222584), Macugen, IM862, Pazopanib (GW786034), ABT-869 and angiozyme.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to BI-2536.

Examples of bcr-abl kinase inhibitors include, but are not limited to, Gleevec (imatinib) and Dasatinib (BMS354825).

Examples of platinum containing agents includes, but are not limited to, cisplatin. Paraplatin (carboplatin), eptaplatin, lobaplatin, nedaplatin, Eloxatin (oxaliplatin) and satraplatin.

Examples of mTOR inhibitors includes, but are not limited to, CCI-779, rapamycin, temsirolimus, everolimus, RAD001 and AP-23573.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FCI, VER49009, IPI-504, SNX-2112 and STA-9090.

Examples of histone deacetylase inhibitors (HDAC) includes, but are not limited to, Suberoylanilide hydroxamic acid (SAHA), MS-275, Valproic acid, TSA, LAQ-824, Trapoxin, and Depsipeptide.

Examples of MEK inhibitors, include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202. R-roscovitine), ZK-304709, PHA-690509. BMI-1040, GPC-286199, BMS-387,032, PD0332991 and AZD-5438.

Examples of useful COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), parecoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033 (canertinib), Herceptin (trastuzumab), Omitarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 tri-functional bispecfic antibodies, mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine (VNP 40101M), temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabine, 5-azacitidine, capecitabine, cladribine, clofarabine, decitabine, eflornithine, ethnylcytidine, cytosine arabinoside, hydroxyurea, TS-1, melphalan, nelarabine, nolatrexed, ocfosate, disodium premetrexed, pentostatin, pelitrexol, raltitrexed, triapine, trimetrexate, vidarabine, mycophenolic acid, tiazofurin, Ribavirin, EICAR, hydroxyurea and deferoxamine.

Examples of antibiotics include intercalating antibiotics but are not limited to, aclarubicin, actinomycin D, amrubicin, annamycin, adriamycin, bleomycin, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, Amsacrine, Cardioxane (Dexrazoxine), diflomotecan, irinotecan HCL (Camptosar), edotecarin, epirubicin (Ellence), etoposide, exatecan, Becatecarin, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGF1R antibodies, chTNT-1/B, Denosumab, Panorex (Edrecolomab), Rencarex (WX G250), Zanolimumab, Lintuzumab, Ticilimumab.

Examples of hormonal therapies include, but are not limited to, exemestane (Aromasin), leuprolide acetate, Buserelin, Cetrorelix, Deslorelin, Vantas, anastrozole (Arimidex), fosrelin (Zoladex), goserelin, Degarelix, doxercalciferol, fadrozole, formestane, tamoxifen citrate (tamoxifen), Arzoxifene, Casodex, Abarelix, Trelstar, finasteride, fulvestrant, toremifene, raloxifene, Trilostane (Modrastane, Desopan), lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Panretin (aliretinoin), Atragen, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MG132, NPI-0052 and PR-171.

Examples of immunologicals include, but are not limited to, interferons and numerous other immune enhancing agents. Interferons include interferon alpha, interferon alpha-2a, interferon alpha-2b, interferon beta, interferon gamma-1a, interferon gamma-1b (Actimmune), or interferon gamma-n1 and combinations thereof. Other agents include Alfaferone (Leukocyte alpha interferon, Cliferon), filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFG1), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofiran, picibanil PF-3512676 (CpG-8954) and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, triacetyluridine Troxacitabine (Troxatyl) and Gemcitabine.

Examples of purine analogs include but are not limited to, Mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, epothilone D (KOS-862), PNU100940 (109881), Batabulin, Ixabepilone (BMS 247550), Patupilone, XRP-9881, Vinflunine and ZK-EPO.

Compounds of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy.

Additionally, compounds having formula (II) may be combined with other antitumor agents selected from the following agents, Genasense, Panitumumab, Zevalin, Bexxar (Corixa), Arglabin, Abarelix, Alimta, EPO906, discodermolide, Neovastat, enzastaurin, Combrestatin A4P, ZD-6126, AVE-8062, DMXAA, Thymitaq, Temodar, Revlimid, Cypat, Histerelin, Plenaizis, Atrasentan, Celeuk (celmoleukin), Satraplatin, thalomide (Thalidomide), theratope, Temilifene, ABI-007, Evista, Atamestane, Xyotax, Targretin, Triazone, Aposyn, Nevastat, Ceplene, Lanreotide, Aredia (pamidronic acid), Orathecin, Virulizin, Gastrimmune, DX-8951f, Mepact (Liposome muramyl tripeptide phophatidylethanolamine, Junovan), Dimericine (Liposome T4 endonuclease V), Onconase, BEC2, Xcytrin, CeaVac, NewTrexin, OvaRex, Osidem, Advexin, RSR13 (efaproxiral, Cotara, NBI-3001 (IL-4), Canvaxin, GMK vaccine, PEG Interferon A, Taxoprexin, gene therapy agents such as TNFerade (GeneVac) or GVAX, Interferon-alpha, Interferon-gamma, Gardasil, Eniluracil (GW 776C85), Lonafarnib, ABT-100, Tumor necrosis factor, Lovastatin, staurosporine, dactinomycin, zorubicin, Bosentan, OncoVAX, Cervarix, Cintredekin besudotox (IL-13-PE38, IL-13-PE38QQR, Interleukin 13-pseudomonas exotoxin), Oncophage (HSPPC 96), Phenoxodiol (NV 06), IGN 101, PANVAC (CEA, MUC-1 vaccinia), ampligen, ibandronic acid, miltefosine, L-asparaginase, procarbazine, Trabectedin (ET-743, Ecteinascidin 743, Yondelis), 5,10-methylenetetrahydrofolate, hydroxycarbamide, pegaspargase, pentostatin, tazarotne, TransMiD 107R (KSB 311), Trisenox, Telcyta, tretinoin, acitretin, Zometa (zolendronic acid), Pandimex (Aglycon protopanaxadiol, PBD-2131), Talabostat (PT100), Tesmilifene, Tetrandrine, halofuginone, rebimastat, removab, squalamine, ukrain, Paditaxel, Zinecard and Vitaxin.

BAX and BAD peptides are reported in Zhang, H. C., Nimmer, P., Rosenberg, S. H., Ng, S. C., and Joseph, M. (2002). Development of a High-Throughput Fluorescence Polarization Assay for Bcl-x(L). Analytical Biochemistry 307, 70-75.

Binding affinity of compounds having formula (II) to Bcl-$X_L$ protein is indicia of their inhibition of the activity of this protein. To determine the binding affinity of compounds having formula (II) to Bcl-$X_L$ protein, representative examples were diluted in DMSO to concentrations between 100 μM and 1 pM and added to each well of a 96-well microtiter plate. A mixture comprising 125 μL per well of assay buffer (20 mM phosphate buffer (pH 7.4), 1 mM EDTA, 50 mM NaCl, 0.05% PF-68), 6 nM of Bcl-$X_L$ protein (prepared as described in Science 1997, 275, 983-986), 1 nM fluorescein-labeled BAD peptide (prepared in-house) and the DMSO solution of the compound was shaken for 2 minutes and placed in a LJL Analyst (LJL Bio Systems, CA). A negative control (DMSO, 15 nM BAD peptide, assay buffer) and a positive control (DMSO, 1 nM BAD peptide, 6 nM Bcl-$X_L$, assay buffer) were used to determine the range of the assay. Polarization was measured at room temperature using a continuous Fluorescein lamp (excitation 485 nm, emission 530 nm). Percentage of inhibition was determined by (1−((mP value of well−negative control)/range))×100%. The results are shown in TABLE 1.

Binding affinity of compounds having formula (II) to Bcl-2 protein is indicia of their inhibition of the activity of this protein. To determine the binding affinity of compounds having formula (II) to Bcl-2, representative examples were diluted in DMSO to concentrations between 10 μM and 10 pM and added to each well of a 96-well microtiter plate. A mixture comprising 125 L per well of assay buffer (20 mM phosphate buffer (pH 7.4), 1 mM EDTA, 50 mM NaCl, 0.05% PF-68), 10 nM of Bcl-2 protein (prepared according to the procedure described in PNAS 2001, 98, 3012-3017), 1 nM fluorescein-labeled BAX peptide (prepared in-house) and the DMSO solution of the representative EXAMPLE was shaken for 2 minutes and placed in a LJL Analyst (LJL Bio Systems, CA. Polarization was measured at room temperature using a continuous Fluorescein lamp (excitation 485 nm, emission 530 nm). The results are also shown in TABLE 1.

These data demonstrate the utility of compounds having formula (II) as binders to and inhibitors of anti-apoptic BCl-$X_L$ protein and anti-apoptotic Bcl-2.

It is expected that, because compounds having formula (II) bind to and inhibit the activity of BCl-$X_L$ and Bcl-2, they would also have utility as inhibitors of anti-apoptotic family protein members having close structural homology to BCl-$X_L$ and Bcl-2 such as, for example, anti-apoptotic Bcl-w protein.

Accordingly, compounds having formula (II) are expected to have utility in treatment of diseases during which anti-apopotic Bcl-$X_L$ protein, anti-apoptotic Bcl-2 protein, anti-apoptotic Bcl-w protein or a combination thereof, are expressed.

Determination of Cellular Efficacy in Human Tumor Cell Line

NCI-H146 (ATCC, Manassas, Va.) human small cell lung carcinoma cells were plated 50,000 cells per well in 96-well tissue culture plates in a total volume of 100 μL, tissue culture medium supplemented with 10% human serum (Invitrogen, Carlsbad, Calif.) instead of fetal bovine serum and treated with a 2-fold serial dilution of the compounds of interest from 10 μM to 0.020 μM. Each concentration was tested in duplicate at least 3 separate times. The number of viable cells following 48 hours of compound treatment was determined using the CellTiter 96® $AQ_{ueous}$ non-radioactive cell proliferation MTS assay according to manufacturer's recommendations (Promega Corp., Madison, Wis.). The results are also shown in TABLE 1.

Pharmacokinetic Evaluation of Selected Compounds in Rat

The pharmacokinetic behavior of compounds of this invention was determined following a single 2 mg/kg intravenous or 5 mg/kg oral dose in male Sprague-Dawley derived rats (n=3 per group). The compounds were prepared as 2 mg/mL solution in a 10% DMSO in PEG-400 formulation for both oral and intravenous administration. The 1 mL/kg intravenous dose was administered as a slow bolus (about 1-2 minutes) in the jugular vein of a rat under light ether anesthetic. The oral dose was administered by gavage. Serial blood samples were obtained from a tail vein of each rat prior 0.1 (IV only), 0.25, 0.5, 1, 1.5, 2, 3, 4, 6, 8 and 24 hours after dosing. The heparinized samples were thoroughly mixed and placed in an ice bath. Plasma was separated by centrifugation and stored frozen prior to analysis. The results are also shown in TABLE 1.

The compounds of interest were separated from the plasma using protein precipitation with acetonitrile. A plasma (100-200 μL, sample or spiked standard) aliquot was combined with 50 μL of internal standard (structurally related analog prepared in acetonitrile) and 1 ml acetonitrile in a 96-well polypropylene deep well plate. The plates were vortexed for 30 seconds followed by centrifugation (3500 rpm×15 minutes, 4° C.). In an automated manner, the supernatant was transferred to a clean 96-well plate. The samples were evaporated to near dryness on a Micro-Vap™ under a stream of dry nitrogen over low heat (~37° C.). The samples were reconstituted vortexing with 0.2 mL 5% DMSO in acetonitrile. A 0.1-0.2 ml aliquot of acetonitrile:0.1% trifluoroacetic acid (20:80, by volume) was added to each well, followed by an additional 30 second vortexing. The plates were centrifuged (3500 rpm×15 minutes, 4° C.) prior to HPLC-MS/MS analysis. Samples were analyzed simultaneously with spiked plasma standards. All samples from each study were analyzed as a single batch on the LC-MS/MS.

The compounds of interest and the internal standard were separated from each other and co-extracted contaminants on a 50×3 mm Keystone Betasil CN 5 μm column with an acetonitrile:0.1% trifluoroacetic acid mobile phase (50:50, by volume) at a flow rate of 0.7 ml/min. Analysis was performed on a Sciex API 300™ Biomolecular Mass Analyzer using a heated nebulizer interface. Peak areas of the title compounds and internal standards were determined using the Sciex Mac-Quan™ software. Calibration curves were derived from peak area ratio (parent drug/internal standard) of the spiked rat plasma standards using least squares linear regression of the ratio versus the theoretical concentration. The methods were generally linear over the range of the standard curve (correlation coefficients >0.99) with an estimated quantitation limit of 0.01 μg/mL. The plasma concentration data for each animal were submitted to multi-exponential curve fitting using WinNonlin. The area under the plasma concentration-time curve from 0 to t hours (time of the last measurable plasma concentration) after dosing ($AUC_{0-t}$) was calculated using the linear trapezoidal rule for the plasma concentration-time profiles. The residual area extrapolated to infinity, determined as the final measured plasma concentration ($C_t$) divided by the terminal elimination rate constant (β), was added to $AUC_{0-t}$ to produce the total area under the curve. The results are also shown in TABLE 1.

TABLE 1

| Ex. | Ki (Bcl-2) | Ki (Bcl-$X_L$) | $EC_{50}$ | $AUC_{0-\infty}$ | AUC/$EC_{50}$ |
|---|---|---|---|---|---|
| 1 | ≤0.001 μM | ≤0.001 μM | 0.0891 μM | 5.01 μM | 56 |
| 2 | ≤0.001 μM | ≤0.001 μM | 0.0291 μM | 7.01 μM | 241 |
| 3 | ≤0.001 μM | ≤0.001 μM | 0.0288 μM | 4.13 μM | 144 |
| 4 | ≤0.001 μM | ≤0.001 μM | 0.0587 μM | 6.34 μM | 108 |
| 5 | ≤0.001 μM | ≤0.001 μM | 0.0388 μM | 2.22 μM | 57 |
| 6 | ≤0.001 μM | ≤0.001 μM | 0.0010 μM | 0.91 μM | 91 |
| 7 | ≤0.001 μM | ≤0.001 μM | 0.0589 μM | 3.87 μM | 66 |
| 8 | ≤0.001 μM | ≤0.001 μM | 0.0212 μM | 1.10 μM | 52 |
| 9 | ≤0.001 μM | ≤0.001 μM | 0.0137 μM | 1.88 μM | 137 |
| 10 | ≤0.001 μM | ≤0.001 μM | 0.0342 μM | 2.48 μM | 73 |
| 11 | ≤0.002 μM | ≤0.003 μM | 0.0206 μM | 2.40 μM | 117 |
| 12 | ≤0.001 μM | ≤0.001 μM | 0.0271 μM | 2.07 μM | 76 |
| 13 | ≤0.001 μM | ≤0.001 μM | 0.0190 μM | 2.06 μM | 108 |
| 14 | ≤0.001 μM | ≤0.001 μM | 0.0309 μM | 3.42 μM | 111 |
| 15 | ≤0.001 μM | ≤0.001 μM | 0.0099 μM | 1.25 μM | 126 |
| 16 | ≤0.002 μM | ≤0.002 μM | 0.0374 μM | 2.37 μM | 63 |
| 17 | ≤0.001 μM | ≤0.001 μM | 0.0287 μM | 0.88 μM | 31 |
| 18 | ≤0.001 μM | ≤0.001 μM | 0.0154 μM | 0.61 μM | 40 |
| 19 | ≤0.001 μM | ≤0.001 μM | 0.0158 μM | 7.12 μM | 451 |
| 20 | ≤0.001 μM | ≤0.001 μM | 0.0277 μM | 3.11 μM | 112 |
| 21 | ≤0.001 μM | ≤0.001 μM | 0.0643 μM | 1.81 μM | 28 |
| 22 | ≤0.001 μM | ≤0.001 μM | 0.0388 μM | 4.08 μM | 105 |
| 23 | ≤0.001 μM | ≤0.001 μM | 0.0528 μM | 3.54 μM | 67 |
| 24 | ≤0.001 μM | ≤0.001 μM | 0.0443 μM | 8.04 μM | 181 |
| 25 | ≤0.001 μM | ≤0.001 μM | 0.0164 μM | 1.67 μM | 102 |
| 26 | ≤0.001 μM | ≤0.001 μM | 0.0243 μM | 0.80 μM | 33 |
| 27 | ≤0.001 μM | ≤0.001 μM | 0.0185 μM | 2.08 μM | 112 |
| 28 | ≤0.001 μM | ≤0.001 μM | 0.0242 μM | 6.30 μM | 260 |
| 29 | ≤0.001 μM | ≤0.001 μM | 0.0298 μM | 1.74 μM | 58 |
| 30 | ≤0.001 μM | ≤0.001 μM | 0.0317 μM | 3.39 μM | 107 |
| 31 | ≤0.001 μM | ≤0.001 μM | 0.0130 μM | 5.10 μM | 392 |
| 32 | ≤0.001 μM | ≤0.001 μM | 0.0187 μM | 1.38 μM | 73.9 |
| 33 | ≤0.001 μM | ≤0.001 μM | 0.0378 μM | 3.01 μM | 79.8 |
| 34 | ≤0.001 μM | ≤0.001 μM | 0.0200 μM | 11.07 μM | 554 |
| 35 | ≤0.001 μM | ≤0.001 μM | 0.0076 μM | 1.26 μM | 166 |
| 36 | ≤0.001 μM | ≤0.001 μM | 0.0242 μM | 4.22 μM | 174 |
| 37 | ≤0.001 μM | ≤0.001 μM | 0.0175 μM | 7.30 μM | 417 |
| 38 | ≤0.001 μM | ≤0.001 μM | 0.0394 μM | 0.67 μM | 17 |
| 39 | ≤0.001 μM | ≤0.001 μM | 0.0827 μM | 1.66 μM | 20 |

The compounds of the present invention were also tested against compounds disclosed in WO 2005/049594, identified herein as EXAMPLES A-L, by determining the ratio of systemic exposure to cellular efficacy. This measure, sometimes reported as $AUC/EC_{50}$, is well known to those skilled in the art of pharmaceutical drug discovery and drug development as a useful pharmacodynamic predictor of oral efficacy.

The examples of the present invention and compounds disclosed in WO 2005/049594 were both tested H146 cellular assay and evaluated for oral pharmacokinetic properties in rat, both as previously described herein. The results are shown in TABLES 2 and 3. As can be seen with reference to the data, the compounds of to the present invention have a more preferred pharmacodynamic profile as compared to the compounds known in the art. From these results a number of observations can be drawn. It can be observed that the compounds having a $NO_2$ moiety at position $W^1$ tend to have good to excellent cellular potency. However, when the pharmacokinetic properties of these same compounds are determined, it can be seen that the systemic exposure after oral administration is poor, resulting in $AUC/EC_{50}$ ratios of from 0.5 to 19.7. On the other hand, when compounds having a $CF_3$ or $CN$ moiety at position $W^1$ are tested in the cellular assay, the results demonstrate that these derivatives have relatively poor cellular efficacy while at the same time having suitable systemic exposure after oral administration. Again, this combination provides overall $AUC/EC_{50}$ ratios from about 2.8 to about <7.4. Surprisingly, compounds of the present invention demonstrate cellular efficacy on par with compounds having an $NO_2$ moiety while maintaining suitable systemic exposure after oral administration. The resulting $AUC/EC_{50}$ ratios for the compounds of the invention are from about 20 to about 554.

TABLE 2

| EXAMPLE | $W^1$ | $W^2$ | $W^3$ | H146, $EC_{50}$, (µM) | $C_{max}$, (µM) | AUC, (µM) | $AUC/EC_{50}$ |
|---|---|---|---|---|---|---|---|
| 38 | $SO_2CF_3$ | $N(CH_3)_2$ | H | 0.039 | 0.072 | 0.665 | 16.9 |
| A | $CF_3$ | $N(CH_3)_2$ | H | 1.599 | 0.371 | 4.412 | 2.8 |
| B | $NO_2$ | $N(CH_3)_2$ | H | 0.063 | 0.039 | 0.283 | 4.5 |
| C | CN | $N(CH_3)_2$ | H | 1.807 | 0.315 | 1.917 | 1.1 |
| D | $CF_3$ | $N(CH_3)_2$ | F | 7.329 | 0.386 | 3.827 | 0.5 |
| 39 | $SO_2CF_3$ | —N(morpholine) | H | 0.083 | 0.290 | 1.657 | 20.0 |
| E | $NO_2$ | —N(morpholine) | H | 0.974 | 0.195 | 1.157 | 1.2 |
| F | $CF_3$ | —N(morpholine) | H | >1.00 | 0.592 | 7.365 | <7.4 |

TABLE 3

| EX-AMPLE | W¹ | W² | H146 EC$_{50}$, (μM) | C$_{max}$, (μM) | AUC, (μM) | AUC/EC$_{50}$ |
|---|---|---|---|---|---|---|
| 18 | SO$_2$CF$_2$Cl | N(CH$_3$)$_2$ | 0.015 | 0.059 | 0.609 | 39.5 |
| 26 | SO$_2$CF$_3$ | N(CH$_3$)$_2$ | 0.024 | 0.097 | 0.803 | 33.0 |
| G | NO$_2$ | N(CH$_3$)$_2$ | 0.026 | 0.057 | 0.507 | 19.7 |
| H | CF$_3$ | N(CH$_3$)$_2$ | 0.410 | 0.215 | 1.973 | 4.8 |
| 3 | SO$_2$CF$_2$Cl | morpholine | 0.029 | 0.385 | 4.131 | 143.6 |
| 7 | SO$_2$CF$_3$ | morpholine | 0.059 | 0.518 | 3.867 | 65.6 |
| 1 | NO$_2$ | morpholine | 0.094 | 0.267 | 1.977 | 21.0 |
| 6 | SO$_2$CF$_2$Cl | 2-oxa-5-azabicyclo | 0.010 | 0.113 | 0.913 | 91.6 |
| 9 | SO$_2$CF$_3$ | 2-oxa-5-azabicyclo | 0.014 | 0.156 | 1.878 | 137.5 |
| J | NO$_2$ | 2-oxa-5-azabicyclo | 0.028 | 0.047 | 0.402 | 14.3 |
| 8 | SO$_2$CF$_3$ | azabicyclo | 0.021 | 0.071 | 1.098 | 51.7 |
| K | NO$_2$ | azabicyclo | 0.049 | 0.077 | 0.368 | 7.5 |
| 33 | SO$_2$CF$_3$ | N(i-Pr)CH$_3$ | 0.038 | 0.129 | 3.013 | 79.8 |
| L | NO$_2$ | N(i-Pr)CH$_3$ | 0.034 | 0.0367 | 0.615 | 18.2 | i-Pr means iso-propyl

Figure 2:
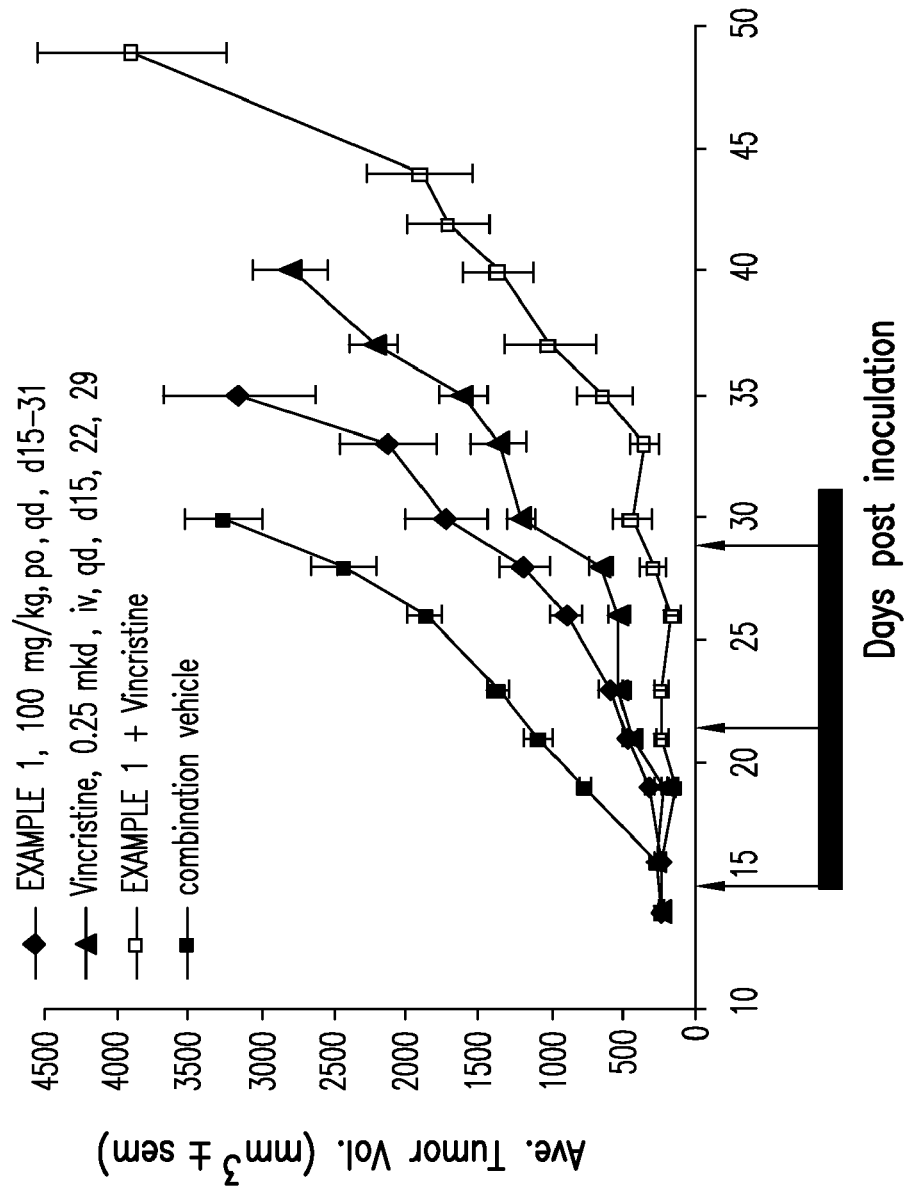
FIG. 2 shows comparitive antitumorgenesis of EXAMPLE 1, vincristine and combinations thereof on B-cell lymphoma.
Figure 3:
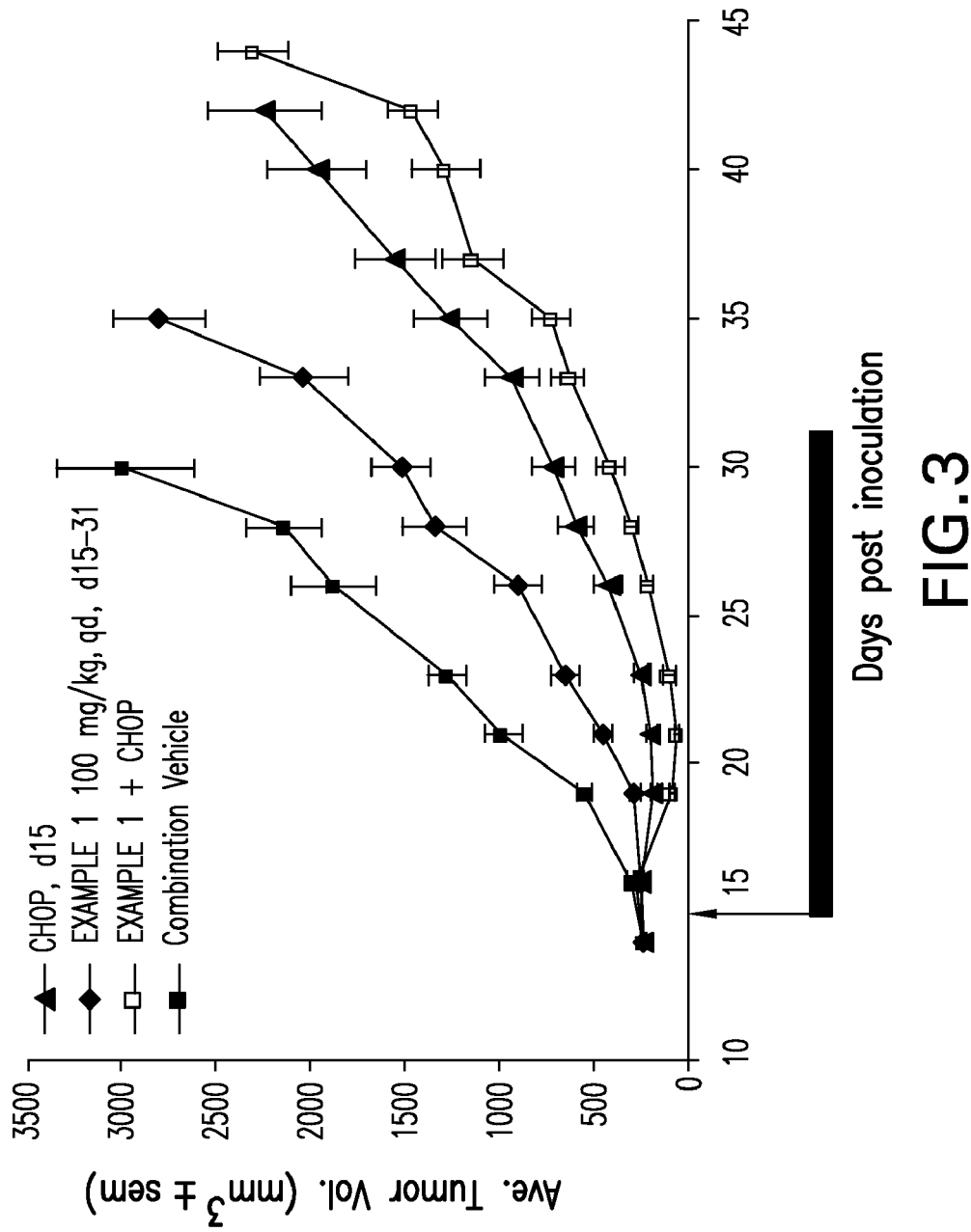
FIG. 3 shows comparitive antitumorgenesis of EXAMPLE 1, CHOP and combinations thereof on B-cell lymphoma.
Figure 4:
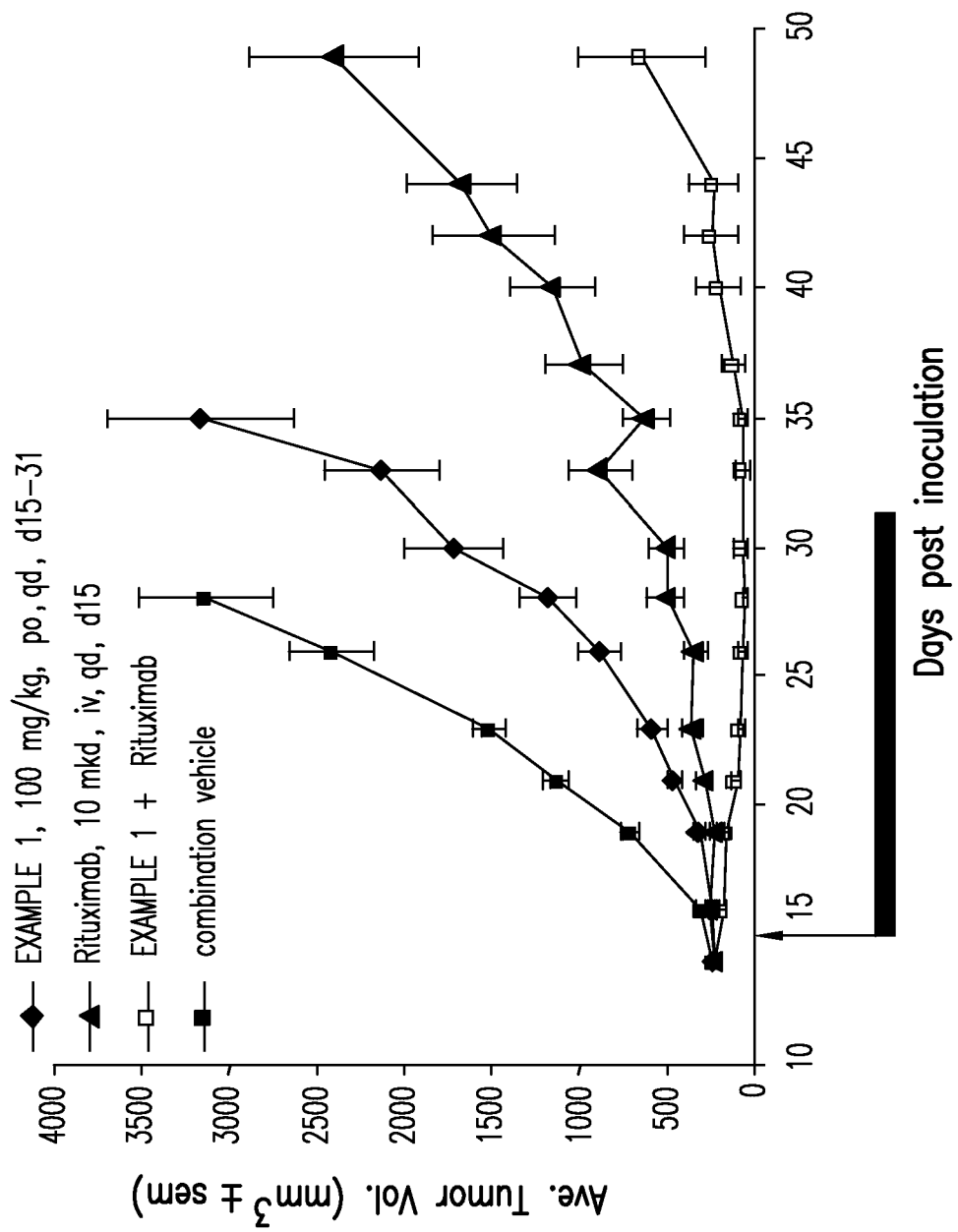
FIG. 4 shows comparitive antitumorgenesis of EXAMPLE 1, rituximab and combinations thereof on B-cell lymphoma.
Figure 5:
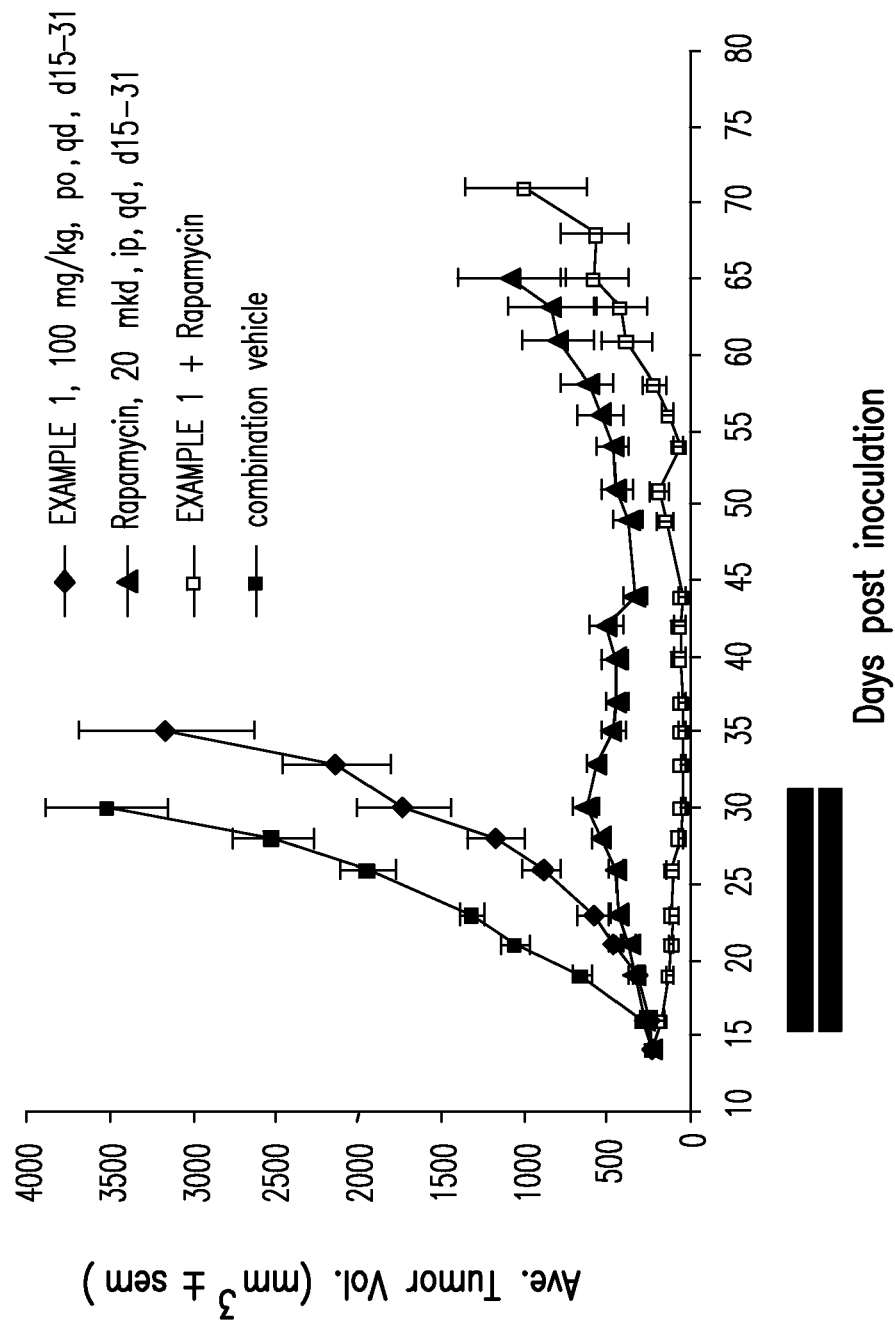
FIG. 5 shows comparitive antitumorgenesis of EXAMPLE 1, rapamycin and combinations thereof on B-cell lymphoma.
Figure 6:
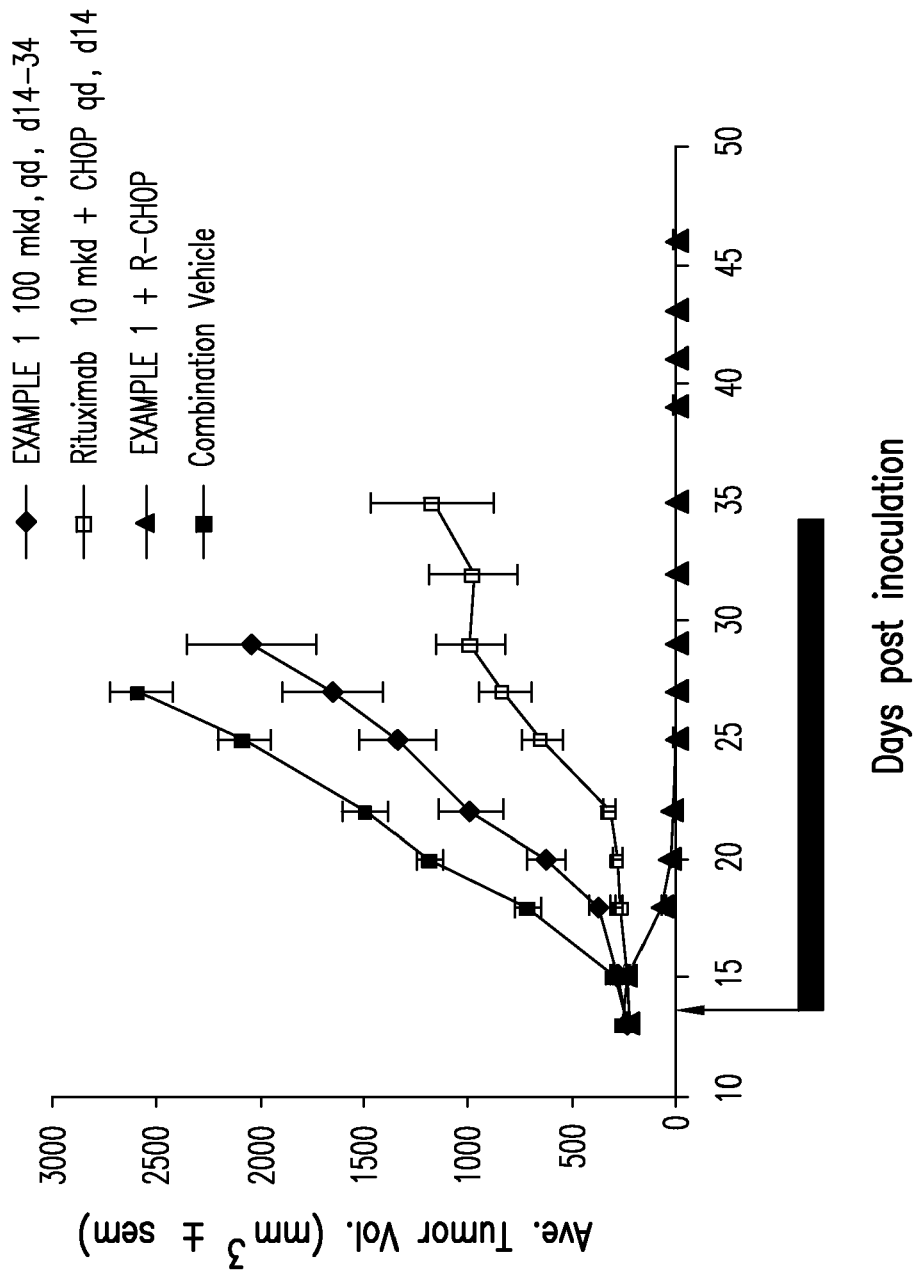
FIG. 6 shows comparitive antitumorgenesis of EXAMPLE 1, R-CHOP and combinations thereof on mantle cell lymphoma.
Figure 7:
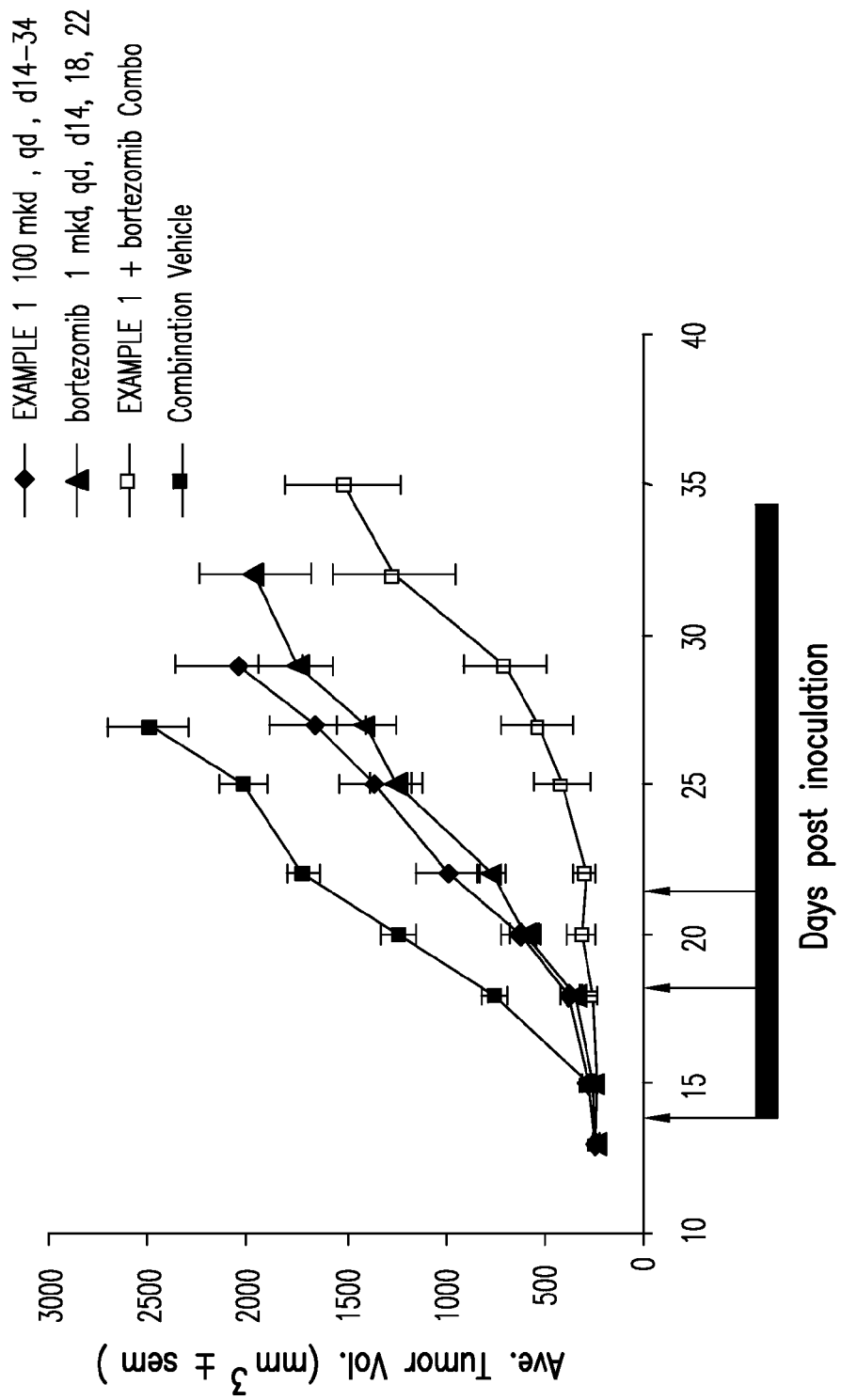
FIG. 7 shows comparitive antitumorgenesis of EXAMPLE 1, bortezomib and combinations thereof on mantle cell lymphoma.

As shown in FIGS. 1-7, studies pertaining to the oral efficacy of EXAMPLE 1 in combination with etoposide, vincristine, CHOP, rituximab, rituximab with CHOP, rapamycin, and velcade demonstrated that EXAMPLE 1 synergistically enhanced efficacy of these cytotoxic agents during combination therapy when administered orally.

Further, combinations comprising EXAMPLE 1 and vincristine resulted in 10% complete tumor regression.

Still further, combinations comprising EXAMPLE 1 and rituximab resulted in 70% complete tumor regression whereas no tumor regressions were observed for rituximab alone.

Still further, combinations comprising EXAMPLE 1 and rapamycin resulted in 70% complete tumor regression whereas 10% tumor regressions were observed for rapamycin alone.

Still further, combinations comprising EXAMPLE 1 and rituximab with CHOP resulted in 90% complete tumor regression whereas 10% tumor regressions were observed for rituximab with CHOP only.

Still further, combinations comprising EXAMPLE 1 and bortexomib resulted in 10% complete tumor regression whereas no tumor regressions were observed for bortexomib alone.

Diseases during which anti-apopotic Bcl-X$_L$ protein, anti-apopotic Bcl-2 protein, anti-apopotic Bcl-w protein or a combination thereof, are expressed include, but are not limited to, cancer and autoimmune disorders, wherein cancer includes, but is not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung carcinoma, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer squamous cell carcinoma, synovioma, sweat gland carcinoma, Waldenström's macroglobulinemia, testicular tumors, uterine cancer and Wilms' tumor, (Cancer Res., 2000, 60, 6101-10 and Medicine, 2d Ed., J.B. Lippincott Co. Philadelphia (1985)); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384: Br. J. Haematol. 2000 September; 110(3): 584-90; Blood 2000 Feb. 15; 95(4):1283-92; and New England Journal of Medicine 2004 September; 351(14): 1409-1418).

It is also expected that compounds having formula (II) would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer), testicular cancer (including germ cell testicular cancer).

It is also expected that compounds having formula (II) would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer (commonly-owned U.S. application Ser. No. 10/988,338), Cancer Res., 2000, 60, 6101-10); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

Compounds having formula (II) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo[3.3.1]nonane; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-$BH_3$ means macroporus triethylammonium methyl polystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl) amine; TEA means triethylamine; TFA means trifluoroacetic acid: THE means tetrahydrofuran; NCS means N-chlorosuccinimide; NMM means N-methylmorpholine; NMP means N-methylpyrrolidine; $PPh_3$ means triphenylphosphine.

SCHEME 1

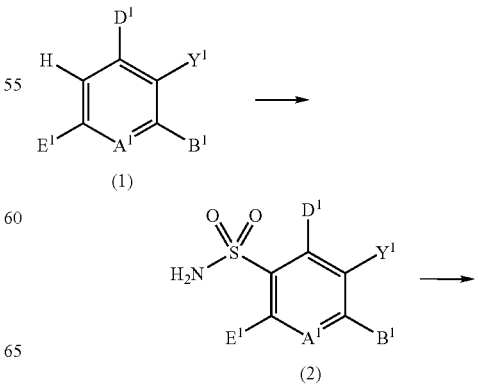

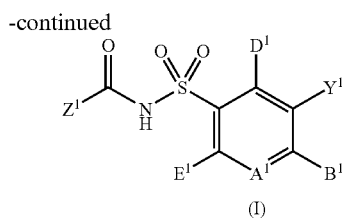

(I)

As shown in SCHEME 1, compounds having formula (1) may be converted to compounds having formula (2) by reacting the former, chlorosulfonic acid, and ammonia.

SCHEME 2

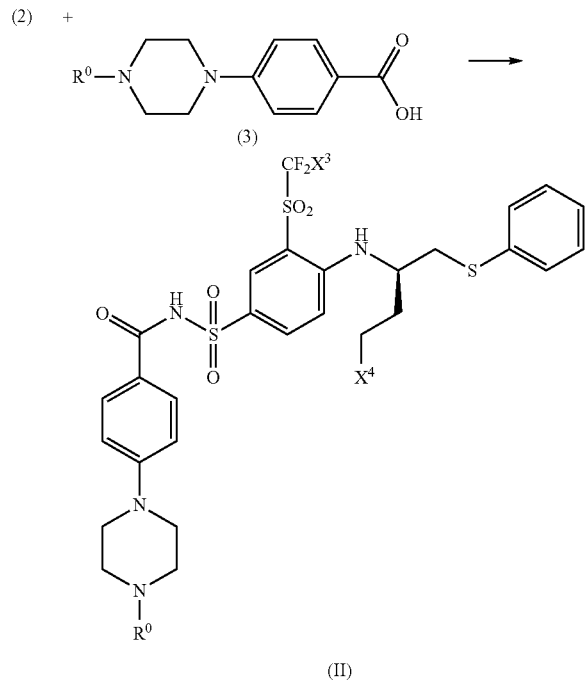

(II)

Compounds having formula (2) may be converted to compounds having formula (II) by reacting the former and compounds having formula (3) and a coupling agent, with or without a base. Examples of coupling agents include EDCI, CDI, and PyBop. Examples of bases include TEA, DIEA, DMAP, and mixtures thereof.

Compounds having formula (2) may be converted to compounds having formula (II) by reacting the former and compounds having formula $Z^1$—COCl and the base.

The following examples are presented to provide what is believed to be the most useful and readily understood description of procedures and conceptual aspects of this invention.

Example 1A 3-(R)-((Carbobenzyloxy)amino)-γ-butyrolactone, prepared as described in J. Am. Chem. Soc. 1986, 108, 4943-4952, (62 g) and morpholine (46 mL) in dioxane (700 mL) at 65° C. was stirred for 24 hours, cooled and concentrated. The concentrate was chromatographed on silica gel with 10% methanol/ethyl acetate.

Example 1B

EXAMPLE 1A (16.5 g), diphenyl disulfide (14.5 g) and tributylphosphine (16.6 mL) in toluene (250 mL) at 80° C. was stirred for 24 hours, cooled and concentrated. The concentrate was chromatographed on silica gel with 1:1 ethyl acetate/hexanes.

Example 1C

EXAMPLE 1B (18 g) in 30% HBr in acetic acid (250 mL) at 25° C. was stirred for 24 hours, concentrated, poured into 1M HCl and extracted with diethyl ether. The extract was extracted with 1M HCl, and this extract was cooled to 0° C. adjusted to pH 12 with KOH and extracted with dichloromethane. The extract was washed with brine and dried ($Na_2SO_4$), filtered and concentrated.

Example 1D

EXAMPLE 1C (45.4 g) in THF (500 mL) at 55° C. was treated with 1M $BF_3$.THF (650 mL) over 2 hours, stirred for 24 hours, cooled to 0° C., treated with methanol (80 mL), poured into methanol (500 mL) and concentrated. A mixture of the concentrate in methanol (400 mL) was treated with a HCl-saturated methanol (800 mL), refluxed for 24 hours, cooled, concentrated, poured into 2M NaOH and extracted with ethyl acetate. The extract was washed with 1M NaOH and brine and dried ($Na_2SO_4$), filtered and concentrated. The concentrate was chromatographed on silica gel with ethyl acetate 10% methanol/ethyl acetate and 10% methanol/10% acetonitrile/5% TEA/75% ethyl acetate.

Example 1E

Methyl viologen hydrochloride (1.17 g) in DMF (80 mL) at 25° C. was saturated with trifluoromethyl iodide, treated with 2-fluorobenzenethiol (9.7 mL) and TEA (20 mL), stirred for 24 hours, diluted with water (240 mL) and extracted with diethyl ether. The extract was washed with 1M NaOH, saturated ammonium chloride and brine and concentrated.

Example 1F

EXAMPLE 1E (17.346 g) in 1:1:2 carbon tetrachloride/acetonitrile/water (800 mL) at 25° C. was treated with sodium periodate (56.8 g) and ruthenium(III) chloride hydrate (183 mg), stirred for 18 hours, diluted with dichloromethane (100 mL) and filtered through diatomaceous earth (Celite®). The filtrate was washed with saturated sodium bicarbonate and extracted with dichloromethane. The extract was washed with brine and dried ($MgSO_4$), filtered and concentrated. The concentrate was filtered through silica gel.

Example 1G

EXAMPLE 1F (37.3 g) in chlorosulfonic acid (32.8 mL) at 120° C. was stirred for 18 hours, cooled to 25° C. and pipetted onto crushed ice. The mixture was extracted with ethyl acetate, and the extract was washed with water and brine and dried ($MgSO_4$), filtered and concentrated.

Example 1H

EXAMPLE 1G (23 g) in isopropanol (706 mL) at −78° C. was treated with ammonium hydroxide (98 mL) over 1 hour, stirred for 1 hour, quenched with 6M HCl (353 mL), warmed to 25° C. and concentrated. The concentrate was mixed with water and extracted with ethyl acetate. The extract was dried (MgSO$_4$), filtered and concentrated. The concentrate was recrystallized from ethyl acetate/hexane.

Example 1I

EXAMPLE 1H (13.48 g) and EXAMPLE 1D (11.56 g) in THF (218 mL) was treated with DIEA (15.1 mL), stirred at 50° C. for 4 hours, cooled, treated with saturated sodium bicarbonate and extracted with ethyl acetate. The extract was dried (MgSO$_4$), filtered and concentrated. The concentrate was recrystallized from hexanes/ethyl acetate.

Example 1J

DMF (10 mL) and chloroform (80 mL) at 3° C. was treated with PBr$_3$ (12 mL), stirred for 20 minutes at 25° C., treated with 4,4-dimethylcyclohexanone (7.15 g) in chloroform (50 mL), stirred for 18 hours, poured onto ice, neutralized with solid sodium bicarbonate and extracted with diethyl ether. The extract was washed with brine and dried (MgSO$_4$), filtered and concentrated. The concentrate was chromatographed on silica gel with 0-10% ethyl acetate/hexanes.

Example 1K

EXAMPLE 1J (1.7 g) and 4-piperazin-1-ylbenzoic acid ethyl ester (1.9 g) in methanol (30 mL) was treated with sodium cyanoborohydride (0.6 g), adjusted to pH 5 with acetic acid, stirred for 18 hours and filtered through diatomaceous earth (Celite®). The filtrate was concentrated, and the concentrate was chromatographed on silica gel on silica gel with 10-30% ethyl acetate/hexanes.

Example 1L

EXAMPLE 1K (1.1 g), 4-chlorophenylboronic acid (0.6 g), 2M Na$_2$CO$_3$ (2 mL) and PdCl$_2$(PPh$_3$)$_2$ (0.1 g) in 7:3:2 DME/water/ethanol (20 mL) was stirred at 85° C. for 18 hours, filtered through diatomaceous earth (Celite®) and concentrated. The concentrate was chromatographed on silica gel with 10-30% ethyl acetate/hexanes.

Example 1M

EXAMPLE 1L (4.59 g) and LiOH (1.25 g) in dioxane (75 mL) and water (10 mL) was stirred at 100° C. for 18 hours, cooled to 25° C. and concentrated. The concentrate was dissolved in water, heated to reflux, neutralized with 1M HCl (28.5 mL), cooled to 25° C. filtered and concentrated.

Example 1N

EXAMPLE 1M (31.5 g), EXAMPLE 1I (39.93 g), EDAC.HCl (20.60 g) and DMAP (13.15 g) in dichloromethane (500 mL) at 25° C. was stirred for 18 hours, diluted with dichloromethane, washed with saturated ammonium chloride and brine and dried (MgSO$_4$), filtered and concentrated. The concentrate was chromatographed on silica gel with 0-10% methanol/ammonia-saturated dichloromethane. $^1$H NMR (300 MHz, DMSO-d$_6$) δ 8.12 (d, 1H), 7.94 (dd, 1H), 7.71 (d, 2H), 7.38 (d, 2H), 7.30 (m, 4H), 7.18 (m, 1H), 7.12 (d, 2H), 6.98 (d, 1H), 6.85 (d, 3H), 4.07 (m, 1H), 3.53 (hr, 4H), 3.28 (m, 12H), 2.44 (m, 8H), 1.99 (m, 3H), 1.80 (m, 1H), 1.44 (t, 2H), 0.97 (s, 6H).

Example 2A

Powdered NaOH (31.2 g), TDA-1 (5 mL) and 2-fluorobenzene thiol (33.6 mL) in benzene (400 mL) was saturated with chlorodifluoromethane, stirred at 80° C. for 30 minutes and filtered through diatomaceous earth (Celite®). The filtrate was washed with saturated NaHCO$_3$ and the water layer was extracted with diethyl ether. The extracts were combined and dried (MgSO$_4$), filtered and concentrated.

Example 2B

EXAMPLE 2A (46 g) in 1:1:2 CCl$_4$/CH$_3$CN/water (1.2 L) at 25° C. was treated with NaIO$_4$ (165.6 g) and RuCl$_3$.xH$_2$O (534 mg), stirred for 18 hours, diluted with dichloromethane and filtered through diatomaceous earth (Celite®). The filtrate was washed with saturated NaHCO$_3$ and dried (Na$_2$SO$_4$), filtered and concentrated. The concentrate was filtered through silica gel.

Example 2C

EXAMPLE 2B (25 g) and NCS (17.55 g) in THF (700 mL) at −78° C. was treated with LHMDS (178.5 mL) over 1 hour, stirred for 1 hour and quenched with ammonium chloride. The mixture was extracted with ethyl acetate, and the extract was washed with brine and dried (MgSO$_4$), filtered and concentrated. The concentrate was chromatographed on silica gel with 0-5% ethyl acetate/hexanes.

Example 2D

EXAMPLE 2C (44 g) in chlorosulfonic acid (36.7 mL) at 120° C. was stirred for 18 hours, cooled to 25° C., pipetted onto crushed ice and extracted with ethyl acetate. The extract was washed with water and brine and dried (MgSO$_4$), filtered and concentrated.

Example 2E

EXAMPLE 2D (22 g) in isopropanol (700 mL) at −78° C. was treated with aqueous ammonia (90 mL) over 1 hour, stirred for another hour, quenched with 6M HCl (300 mL), warmed to 25° C. and concentrated. The concentrate was mixed with water and extracted with ethyl acetate. The extract was dried (MgSO$_4$), filtered and concentrated. The concentrate was recrystallized from hexanes/ethyl acetate.

Example 2F

EXAMPLE 2E (2.89 g) and EXAMPLE 1D (2.39 g) in THF (20 mL) was treated with diisopropylethylamine (3.2 mL), stirred at 60° C. for 18 hours, cooled, treated with saturated sodium bicarbonate and extracted with ethyl acetate. The extract was dried (MgSO$_4$), filtered and concentrated. The concentrate was chromatographed on silica gel with 1.5-5% 7M ammonia in methanol/dichloromethane.

Example 2G

Hexane-washed 60% oily NaH (17 g) in dichloromethane (300 mL) at −5° C. was treated with 4,4-dimethyl-2-oxo-cyclohexanecarboxylic acid methylester, prepared as described in Tetrahedron (1992), 48 (21), 4459-64, (53.89 g), stirred for 30 minutes, cooled to −78° C., treated with trifluoromethanesulfonic anhydride, warmed to 25° C., stirred for 18 hours, washed with brine and dried (MgSO$_4$), filtered and concentrated.

Example 2H

EXAMPLE 2G (86 g), 4-chlorophenylboronic acid (50 g), CsF (104 g) and tetrakis(triphenylphosphine)palladium(0)

(2.5 g) in 2:1 DME/methanol (600 mL) at 70° C. was stirred for 18 hours and concentrated. The concentrate was dissolved in diethyl ether, and the solution was dried (MgSO$_4$), filtered and concentrated. The concentrate was filtered through silica gel with 20% ethyl acetate/hexanes.

Example 2I

Lithium borohydride (18 g) was treated with EXAMPLE 2H (76 g) in diethyl ether (400 mL) and methanol (23 mL), stirred at reflux for 4 hours, cooled, quenched with 1M HCl, diluted with water and extracted with diethyl ether. The extract was dried (MgSO$_4$), filtered and concentrated. The concentrate was chromatographed on silica gel with 0-30% ethyl acetate/hexanes.

Example 2J

EXAMPLE 2I (17.5 g) in dichloromethane (100 mL) at 0° C. was treated simultaneously with methanesulfonyl chloride (5.6 mL) and TEA (21 mL), stirred for 5 minutes, treated with 4-piperazin-1-ylbenzoic acid ethyl ester (17 g), stirred at 25° C. for 18 hours, washed with ammonium chloride and dried (Na$_2$SO$_4$), filtered and concentrated. The concentrate was chromatographed on silica gel with 10% ethyl acetate/hexanes.

Example 2K

This example was prepared by substituting EXAMPLE 2J for EXAMPLE 1L in EXAMPLE 1M.

Example 2L

EXAMPLE 2K (16.9 g) and EXAMPLE 2F (22 g) in dichloromethane (200 mL) at 25° C. was treated with EDAC.HCl (11.06 g) and DMAP (7.06 g), stirred for 18 hours, diluted with dichloromethane (400 mL), washed with saturated ammonium chloride and brine and dried (MgSO$_4$), filtered and concentrated. The concentrate was chromatographed on silica gel with 0-10% methanol/ammonia-saturated dichloromethane. $^1$H NMR (400 MHz, DMSO-d$_6$) δ 8.07 (d, 1H), 7.90 (dd, 1H), 7.71 (d, 2H), 7.36 (m, 4H), 7.29 (m, 2H), 7.20 (m, 1H), 7.09 (d, 2H), 6.86 (d, 1H), 6.80 (d, 2H), 6.76 (d, 1H), 4.02 (m, 1H), 3.50 (m, 4H), 3.33 (m, 2H), 3.16 (m, 4H), 2.81 (s, 2H), 2.29 (m, 12H), 1.99 (s, 2H), 1.94 (m, 1H), 1.71 (m, 1H), 1.42 (t, 2H), 0.96 (s, 6H).

Example 3A

This example was prepared by substituting 2-bromo-cyclohex-1-enecarbaldehyde, prepared as described in Collect. Czech. Chem. Commun., 1961, 26, 3059.) for EXAMPLE 1J in EXAMPLE 1K.

Example 3B

This example was prepared by substituting EXAMPLE 3A for EXAMPLE 1K in EXAMPLE 1L.

Example 3C

This example was prepared by substituting EXAMPLE 3B for EXAMPLE 1L in EXAMPLE 1M.

Example 3D

This example was prepared by substituting EXAMPLE 3C and EXAMPLE 2F for EXAMPLE 1M and EXAMPLE 1I, respectively, in EXAMPLE 1N. $^1$H NMR (400 MHz, DMSO-d$_6$) δ 8.11 (d, 1H), 7.92 (dd, 1H), 7.71 (d, 2H), 7.37 (d, 2H), 7.34 (m, 2H), 7.27 (t, 2H), 7.18 (t, 1H), 7.12 (d, 2H), 6.94 (d, 1H), 6.84 (m, 3H), 4.04 (m, 1H), 3.51 (br, 4H), 3.27 (br, 10H), 2.84 (br, 2H), 2.33 (br, 6H), 2.18 (br, 4H), 1.97 (m, 1H), 1.76 (m, 1H), 1.66 (s, 4H).

Example 4A

A solution of 3-(R)-((carbobenzyloxy)amino)-γ-butyrolactone (prepared according to the procedure described in J. Am. Chem. Soc. 1986, 108, 4943-4952, 7.72 g, 32.8 mmol) in THF (100 mL) was saturated with gaseous dimethylamine, stirred at room temperature for 16 hours, and concentrated. The residue was filtered through a plug of silica gel eluting with 50% acetone in hexanes to give the desired product.

Example 4B

A solution of EXAMPLE 4A (8.45 g, 30.14 mmol) in toluene (15 mL) was treated with tributylphosphine (9.76 mL, 39.20 mmol) and diphenyldisulfide (7.30 g, 39.20 mmol) and heated to 80° C. for 16 hours. The reaction mixture was concentrated and purified by column chromatography on silica gel eluting with a gradient of 0-50% ethyl acetate in hexanes to give the desired product.

Example 4C

EXAMPLE 4B (7.5 g) and bis(cyclopentadienyl)zirconium(IV) chloride hydride (10.31 g) in THF (100 mL) at 25° C. was stirred for 20 minutes and concentrated. The concentrate was chromatographed on silica gel with 50% ethyl acetate in hexane.

Example 4D

EXAMPLE 4C (2.87 g) and N-isopropylmethylamine (1.92 g) in 1,2-dichloroethane (50 mL) at 25° C. was treated with sodium triacetoxyborohydride (3 g), stirred for 2 hours, diluted with ethyl acetate, washed with 2M NaOH, water and brine and dried (Na$_2$SO$_4$), filtered and concentrated. The concentrate was chromatographed on silica gel with 1% methanol/dichloromethane.

Example 4E

This example was prepared by substituting EXAMPLE 4D for EXAMPLE 1B in EXAMPLE 1C.

Example 4F

This example was prepared by substituting EXAMPLE 4E for EXAMPLE 1D in EXAMPLE 1I.

Example 4G

This example was prepared by substituting EXAMPLE 4F for EXAMPLE 1I in EXAMPLE 1N. $^1$H NMR (400 MHz, DMSO-d$_6$) δ 8.08 (s, 1H), 7.98 (d, 1H), 7.71 (d, 2H), 7.37 (m, 4H), 7.28 (t, 2H), 7.20 (t, 1H), 7.12 (d, 2H), 6.89 (d, 1H), 6.78 (d, 2H), 6.70 (d, 1H), 4.01 (m, 1H), 3.13 (m, 6H), 2.75 (m, 2H), 2.28 (m, 6H), 2.04 (m, 4H), 1.99 (m, 2H), 1.43 (m, 2H), 1.12 (m, 10H), 0.97 (s, 6H).

Example 5

This example was prepared by substituting 4-(4-(2-(4-chlorophenyl)cyclo-1-enylmethyl)piperazin-1-yl)benzoic acid, prepared as described in commonly-owned U.S. patent application Ser. No. 10/988,338, and EXAMPLE 4F for EXAMPLE 1M and EXAMPLE 1I, respectively, in EXAMPLE 1N. $^1$H NMR (400 MHz, DMSO-d$_6$) δ 9.00 (m, 1H), 8.09 (s, 1H), 7.98 (d, 1H), 7.71 (d, 2H), 7.36 (m, 4H), 7.30 (t, 2H), 7.20 (t, 1H), 7.09 (d, 2H), 6.90 (d, 1H), 6.78 (d, 2H), 6.65 (d, 1H), 4.00 (m, 2H), 3.13 (m, 4H), 2.78 (m, 2H), 2.55 (m, 2H), 2.40 (m, 4H), 2.31 (m, 4H), 2.00 (m, 3H), 1.79 (m, 4H), 1.58 (m, 4H), 1.51 (m, 2H), 1.12 (m, 6H).

Example 6A

This example was prepared by substituting EXAMPLE 4B for EXAMPLE 1B in EXAMPLE 1C.

Example 6B

EXAMPLE 6A (6.13 g) in THF (200 mL) at 25° C. was treated with di-tert-butyldicarbonate (7 g), stirred for 4 hours and concentrated. The concentrate was dissolved into ethyl acetate (500 mL), washed with 1M NaOH, water and brine and dried (Na$_2$SO$_4$), filtered and concentrated. The concentrate in THF (200 mL) at 25° C. to was treated with 1M NaOH (200 stirred for 5 hours and isolated. The water layer was extracted with ethyl acetate, and the THF and ethyl acetate extracts were combined, washed with water and brine and dried (Na$_2$SO$_4$), filtered and concentrated.

Example 6C

This example was prepared by substituting EXAMPLE 6B for EXAMPLE 5B in EXAMPLE 4C.

Example 6D

This example was prepared by substituting EXAMPLE 6C and 2-oxa-5-aza-bicyclo[2.2.1]heptane, prepared as described in commonly-owned U.S. patent application Ser. No. 10/988,338, for EXAMPLE 4C and N-isopropylmethyl amine in EXAMPLE 4D.

Example 6E

EXAMPLE 6D (7.86 g) in dichloromethane (200 mL) at 25° C. was treated with 2M HCl in diethyl ether (200 mL), stirred for 18 hours and concentrated.

Example 6F

This example was prepared by substituting EXAMPLE 6E for EXAMPLE 1D in EXAMPLE 2F.

Example 6G

This example was prepared by substituting EXAMPLE 6F and EXAMPLE 3C for EXAMPLE 1I and EXAMPLE 1M in EXAMPLE 1N. $^1$H NMR (300 MHz. DMSO-d$_6$) δ 8.07 (s, 1H), 7.92 (d, 1H), 7.70 (d, 2H), 7.37 (m, 4H), 7.30 (t, 2H), 7.21 (t, 1H), 7.12 (d, 2H), 6.84 (d, 1H), 6.79 (d, 2H), 4.21 (m, 1H), 4.09 (m, 1H), 4.01 (m, 2H), 3.82 (m, 2H), 3.46 (m, 1H), 3.18 (m, 6H), 2.86 (m, 4H), 2.75 (m, 4H), 2.28 (m, 2H), 2.18 (m, 4H), 1.88 (m, 4H), 1.66 (m, 4H).

Example 7

This example was prepared by substituting EXAMPLE 3C for EXAMPLE 1M in EXAMPLE 1N. $^1$H NMR (300 MHz, DMSO-d$_6$) δ 8.09 (d, 1H), 7.92 (dd, 1H), 7.71 (d, 2H), 7.31 (m 7H), 7.18 (tt, 1H), 7.12 (dt, 2H), 6.92 (d, 1H), 6.82 (m, 3H), 4.04 (m, 1H), 3.51 (m, 4H), 3.26 (m, 10H), 2.82 (m, 2H), 2.30 (m, 10H), 1.94 (m, 1H), 1.72 (m, 5H).

Example 8A

A solution of 3-(9H-fluoren-9-ylmethoxycarbonylamino)-4-phenylsulfanylbutyric acid, prepared as described in commonly-owned U.S. patent application Ser. No. 10/988,338 and HATU in DMF was treated with 7-aza-bicyclo[2.2.1]heptane (prepared as described in Org. Lett., 2001, 3, 1371-1374; and N-methylmorpholine, stirred at ambient temperature for 30 min, diluted with ethyl acatate, washed with 1.5% HCl, NaHCO$_3$(aq), H$_2$O and brine, dried (Na$_2$SO$_4$), filtered and concentrated to give the desired product.

Example 8B

A solution of EXAMPLE 8A in THF was treated with diethyl amine, stirred at ambient temperature for 2 hours and concentrated. The residue was purified by silica gel chromatography eluting with CH$_2$Cl$_2$ (saturated with NH$_3$), followed by ethyl acetate to give the desired product.

Example 8C

This example was prepared by substituting EXAMPLE 8B for EXAMPLE 1C in EXAMPLE 1D.

Example 8D

This example was prepared by substituting EXAMPLE 8C for EXAMPLE 1D in EXAMPLE 1I.

Example 8E

This example was prepared by substituting EXAMPLE 8D and EXAMPLE 3C for EXAMPLE 1I and EXAMPLE 1M, respectively, in EXAMPLE 1N. $^1$H NMR (300 MHz. DMSO-d$_6$) δ 9.19 (m, 1H), 8.07 (d, 1H), 7.97 (d, 1H), 7.71 (d, 2H), 7.31 (m 6H), 7.20 (tt, 1H), 7.12 (dt, 2H), 6.89 (d, 1H), 6.76 (d, 2H), 6.65 (d, 1H), 4.03 (m, 2H), 3.31 (m, 4H), 3.12 (m, 4H), 2.90 (br, 2H), 2.76 (m 2H), 1.96 (m, 21H).

Example 9A

This example was prepared by substituting EXAMPLE 6E for EXAMPLE 1D in EXAMPLE 1I.

Example 9B

This example was prepared by substituting EXAMPLE 9A and EXAMPLE 3C for EXAMPLE 1I and EXAMPLE 1M, respectively, in EXAMPLE 1N. $^1$H NMR (300 MHz, DMSO-d$_6$) δ 8.08 (d, 1H), 7.94 (d, 17.71 (d, 2H), 7.32 (m 7H), 7.20 (tt, 1H), 7.12 (dt, 2H), 6.87 (d, 1H), 6.78 (d, 3H), 4.40 (m, 1H), 4.03 (m, 2H), 3.83 (m, 2H), 3.54 (m, 2H), 3.26 (m, 2H), 3.14 (m, 4H), 2.80 (br, 2H), 2.78 (m, 4H), 1.97 (m, 14H).

Example 10

This example was prepared by substituting EXAMPLE 9A for EXAMPLE 1I in EXAMPLE 1N. $^1$H NMR (300 MHz, DMSO-d$_6$) δ 8.09 (d, 1H), 7.95 (d, 1H), 7.71 (d, 2H), 7.33 (m 7H), 7.20 (tt, 1H), 7.12 (dt, 2H), 6.90 (d, 1H), 6.79 (d, 3H), 4.44 (m, 1H), 4.03 (m, 1H), 3.84 (m, 1H), 3.57 (m, 1H), 3.02 (m, 13H), 2.25 (m, 6H), 1.99 (m, 6H), 1.43 (t, 2H), 0.97 (s, 6H).

Example 11

This example was prepared by substituting EXAMPLE 6F for EXAMPLE 1I in EXAMPLE 1N. $^1$H NMR (300 MHz, DMSO-$d_6$) δ 8.07 (d, 1H), 7.93 (d, 1H), 7.70 (d, 2H), 7.33 (m 7H), 7.20 (tt, 1H), 7.12 (dt, 2H), 6.81 (m, 4H), 4.41 (m, 1H), 4.06 (m, 1H), 3.83 (m, 1H), 3.47 (m, 1H), 3.02 (m, 13H), 2.25 (m, 6H), 1.99 (m, 6H), 1.43 (t, 2H), 0.97 (s, 6H).

Example 12

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 9A for EXAMPLE 1M and EXAMPLE 1I, respectively, in EXAMPLE 1N. $^1$H NMR (300 MHz, DMSO-$d_6$) δ 8.09 (d, 1H), 7.95 (dd, 1H), 7.71 (d, 2H), 7.32 (m 7H), 7.19 (tt, 1H), 7.09 (dt, 2H), 6.90 (d, 1H), 6.79 (d, 3H), 4.45 (m, 1H), 4.03 (m, 2H), 3.85 (m, 2H), 3.55 (m, 2H), 3.04 (m, 8H), 2.34 (m, 8H), 1.85 (m, 7H), 1.54 (m, 5H).

Example 13

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 6F for EXAMPLE 1M and EXAMPLE 1I, respectively, in EXAMPLE 1N. $^1$H NMR (300 MHz, DMSO-$d_6$) δ 8.07 (d, 1H), 7.93 (dd, 1H), 7.71 (d, 2H), 7.32 (m 7H), 7.20 (tt, 1H), 7.09 (dt, 2H), 6.87 (d, 1H), 6.79 (d, 3H), 4.45 (m, 1H), 4.02 (m, 2H), 3.84 (m, 2H), 3.56 (m, 2H), 3.07 (m, 8H), 2.33 (m, 8H), 1.85 (m, 7H), 1.54 (m, 5H).

Example 14

This example was prepared by substituting EXAMPLE 2K and EXAMPLE 4F for EXAMPLE 1M and EXAMPLE 1I, respectively, in EXAMPLE 1N. $^1$H NMR (300 MHz, DMSO-$d_6$) δ 8.07 (d, 1H), 7.96 (dd, 1H), 7.71 (d, 2H), 7.33 (m 7H), 7.20 (tt, 1H), 7.09 (dt, 2H), 6.87 (d, 1H), 6.77 (d, 2H), 6.72 (d, 1H), 4.00 (m, 1H), 3.28 (m, 4H), 3.12 (m, 4H), 2.79 (m, 2H), 2.48 (m, 2H), 2.23 (m, 8H), 2.02 (m, 4H), 1.42 (t, 2H), 1.08 (m, 6H), 0.96 (s, 6H).

Example 15A

This example was prepared by substituting EXAMPLE 6C and 1,4-oxazepane for EXAMPLE 4C and N-isopropyl-N-methylamine in EXAMPLE 4D.

Example 15B

This example was prepared by substituting EXAMPLE 15A for EXAMPLE 6D in EXAMPLE 6E.

Example 15C

This example was prepared by substituting EXAMPLE 15B for EXAMPLE 1D in EXAMPLE 1I.

Example 15D

This example was prepared by substituting EXAMPLE 15C and EXAMPLE 3C for EXAMPLE 1I and EXAMPLE 1M, respectively, in EXAMPLE 1N. $^1$H NMR (400 MHz, CDCl$_3$) δ 8.32 (s, 1H), 8.01 (br, 1H), 7.67 (d, 2H), 7.34 (t, 4H), 7.24 (m, 3H), 6.99 (m, 3H), 6.67 (br, 3H), 3.97 (br, 1H), 3.88 (s, 2H), 3.79 (s, 2H), 3.73-3.23 (br m, 12H), 3.14 (m, 6H), 2.29 (s, 6H), 2.08 (m, 2H), 1.74 (s, 4H).

Example 16A

This example was prepared by substituting azepane for N-isopropyl-N-methylamine in EXAMPLE 4D.

Example 16B

This example was prepared by substituting EXAMPLE 16A for EXAMPLE 4D in EXAMPLE 4E.

Example 16C

This example was prepared by substituting EXAMPLE 16A for EXAMPLE 1D in EXAMPLE 1I.

Example 16D

This example was prepared by substituting EXAMPLE 16C and EXAMPLE 3C for EXAMPLE 1I and EXAMPLE 1M, respectively, in EXAMPLE 1N. $^1$H NMR (400 MHz, CDCl$_3$) δ 8.33 (s, 1H), 8.01 (d, 1H), 7.67 (d, 2H), 7.34 (t, 4H), 7.23 (m, 3H), 6.98 (m, 3H), 6.67 (m, 3H), 3.99 (m, 1H), 3.82-3.19 (br m, 10H), 3.12 (s, 4H), 2.86 (m, 2H), 2.55 (br, 2H), 2.29 (s, 4H), 2.06 (m, 1H), 1.93 (m, 3H), 1.74 (s, 8H), 1.60 (m, 2H).

Example 17A

This example was prepared by substituting EXAMPLE 6A for EXAMPLE 1C in EXAMPLE 1D.

Example 17B

This example was prepared by substituting EXAMPLE 17B for EXAMPLE 1D in EXAMPLE 1I.

Example 17C

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 17B for EXAMPLE 1M and EXAMPLE 1I, respectively, in EXAMPLE 1N. $^1$H NMR (400 MHz, DMSO-$d_6$) δ 9.58 (brs, 1H), 9.46 (brs, 1H), 8.18 (d, 1H), 8.00 (dd, 1H), 7.77 (d, 2H), 7.41 (d, 2H), 7.29 (d, 2H), 7.24 (m, 2H), 7.13 (m, 4H), 6.96 (m, 3H), 4.12 (m, 1H), 3.87 (m, 1H), 3.63 (m, 1H), 3.38 (m, 4H), 3.15 (m, 4H), 3.02 (m, 2H), 2.74 (s, 6H), 2.46 (m, 4H), 2.09 (m, 2H), 1.81 (m, 2H), 1.57 (m, 4H).

Example 18A

This example was prepared by substituting EXAMPLE 2E and EXAMPLE 17B for EXAMPLE 1H and EXAMPLE 1D in EXAMPLE 1I.

Example 18B

This example was prepared by substituting EXAMPLE 18A and EXAMPLE 3C for EXAMPLE 1I and EXAMPLE 1M, respectively, in EXAMPLE 1N. $^1$H NMR (400 MHz, DMSO-d$_6$) δ 9.60 (brs, 1H), 9.47 (brs, 1H), 8.18 (d, 1H), 7.99 (dd, 1H), 7.77 (d, 2H), 7.41 (d, 2H), 7.30 (d, 2H), 7.24 (m, 2H), 7.15 (m, 3H), 7.12 (d, 1H), 6.96 (m, 3H), 6.92 (d, 1H), 4.10 (m, 1H), 3.91 (m, 2H), 3.60 (m, 2H), 3.37 (m, 4H), 3.15 (m, 2H), 3.02 (m, 1H), 2.74 (s, 6H), 2.25 (d, 4H), 2.08 (m, 2H), 1.71 (m, 4H).

Example 19

This example was prepared by substituting EXAMPLE 2F for EXAMPLE 1I in EXAMPLE 1N. $^1$H NMR (400 MHz, DMSO-d$_6$) δ 8.11 (d, 1H), 7.93 (dd, 1H), 7.71 (d, 2H), 7.36 (m, 4H), 7.27 (m, 2H), 7.18 (m, 1H), 7.12 (d, 2H), 6.97 (d, 1H), 6.85 (m, 3H), 4.05 (m, 1H), 3.53 (m, 4H), 3.23 (m, 1H), 2.83 (m, 1H), 2.34 (m, 8H), 2.22 (m, 2H), 1.99 (m, 2H), 1.96 (m, 1H), 1.77 (m, 1H), 1.44 (t, 2H), 0.97 (s, 6H).

Example 20

This example was prepared by substituting EXAMPLE 17B for EXAMPLE 1I in EXAMPLE 1N. $^1$H NMR (500 MHz, DMSO-d$_6$) δ 9.46 (brs, 1H), 8.18 (d, 1H), 7.99 (dd, 1H), 7.76 (d, 2H), 7.40 (d, 2H), 7.29 (d, 2H), 7.23 (t, 2H), 7.14 (s, 4H), 6.95 (m, 3H), 4.11 (m, 1H), 3.88 (m, 2H), 3.58 (m, 4H), 3.08 (m, 4H), 2.73 (s, 6H), 2.27 (m, 2H), 2.08 (m, 2H), 2.02 (s, 2H), 1.47 (t, 2H), 1.00 (s, 6H).

Example 21

This example was prepared by substituting 4-(4-(4-(4-chlorophenyl)-5,6-dihydro-2H-pyran-3-ylmethyl)piperazin-1-yl)benzoic acid, prepared as described in commonly-owned U.S. patent application Ser. No. 10/988,338, for EXAMPLE 1M in EXAMPLE 1N. $^1$H NMR (400 MHz, DMSO-d$_6$) δ 8.27 (d, 1H), 8.11 (d, 1H), 7.89 (d, 2H), 7.59 (d, 2H), 7.48 (m, 4H), 7.37 (m, 3H), 7.13 (m, 1H), 7.01 (m, 3H), 4.35 (s, 2H), 4.24 (m, 1H), 3.97 (m, 2H), 3.68 (m, 4H), 3.36 (m, 6H), 3.07 (m, 3H), 2.68 (s, 2H), 2.59 (m, 4H), 2.14 (m, 2H), 1.93 (m, 2H).

Example 22A

This example was prepared by substituting EXAMPLE 4E for EXAMPLE 2E in EXAMPLE 2F.

Example 22

This example was prepared by substituting EXAMPLE 2K and EXAMPLE 22A for EXAMPLE 1M and EXAMPLE 1I, respectively, in EXAMPLE 1N. $^1$H NMR (400 MHz, DMSO-d$_6$) δ 9.21 (brs, 1H), 8.17 (m, 1H), 8.00 (dd, 1H), 7.77 (d, 2H), 7.42 (m, 2H), 7.31 (m, 2H), 7.24 (m, 2H), 7.14 (m, 4H), 6.97 (m, 3H), 4.11 (m, 1H), 3.90 (m, 1H), 3.12 (m, 6H), 2.84 (m, 3H), 2.63 (m, 3H), 2.25 (m, 2H), 2.07 (m, 4H), 1.49 (t, 2H), 1.16 (m, 6H), 0.97 (s, 6H).

Example 23

This example was prepared by substituting EXAMPLE 22A for EXAMPLE 1I in EXAMPLE 1N. $^1$H NMR (400 MHz, DMSO-d$_6$) δ 9.21 (brs, 1H), 8.18 (m, 1H), 7.99 (dd, 1H), 7.78 (d, 2H), 7.40 (d, 2H), 7.30 (d, 2H), 7.24 (m, 2H), 7.15 (m, 4H), 6.97 (m, 3H), 4.11 (m, 1H), 3.89 (m, 1H), 3.13 (m, 6H), 2.84 (m, 2H), 2.63 (m, 3H), 2.28 (m, 2H), 2.07 (m, 4H), 1.48 (t, 2H), 1.17 (m, 6H), 1.00 (s, 6H).

Example 24

This example was prepared by substituting EXAMPLE 2K for EXAMPLE 1M in EXAMPLE 1N. $^1$H NMR (500 MHz, DMSO-d$_6$) δ 12.14 (brs, 1H), 9.89 (brs, 1H), 9.52 (s, 1H), 8.18 (d, 1H), 8.00 (dd, 1H), 7.77 (d, 2H), 7.41 (d, 2H), 7.30 (d, 2H), 7.24 (t, 2H), 7.14 (m, 4H), 6.96 (m, 3H), 4.12 (m, 1H), 3.93 (m, 3H), 3.63 (m, 4H), 2.93 (m, 10H), 2.24 (m, 2H), 2.09 (m, 4H), 1.48 (t, 2H), 0.97 (s, 6H).

Example 25

This example was prepared by substituting EXAMPLE 2K and EXAMPLE 6F for EXAMPLE 1M and EXAMPLE 1I, respectively, in EXAMPLE 1N. $^1$H NMR (500 MHz, DMSO-d$_6$) δ 9.58 (brs, 1H), 9.39 (brs, 1H), 8.17 (s, 1H), 7.99 (dd, 1H), 7.77 (d, 2H), 7.41 (d, 2H), 7.30 (d, 2H), 7.24 (t, 2H), 7.14 (m, 4H), 6.97 (m, 3H), 4.63 (d, 1H), 4.43 (d, 1H), 4.13 (m, 1H), 3.92 (m, 2H), 3.69 (m, 2H), 3.52 (m, 2H), 3.01 (m, 6H), 2.25 (m, 2H), 2.04 (m, 6H), 1.49 (m, 2H), 0.98 (s, 6H).

Example 26

This example was prepared by substituting EXAMPLE 17B and EXAMPLE 3C for EXAMPLE 1I and EXAMPLE 1M, respectively, in EXAMPLE 1N. $^1$H NMR (500 MHz, DMSO-d$_6$) δ 9.49 (hrs, 1H), 8.08 (d, 1H), 7.95 (dd, 1H), 7.71 (d, 2H), 7.36 (m, 4H), 7.30 (t, 2H), 7.20 (t, 1H), 7.12 (d, 2H), 6.84 (m, 2H), 6.78 (d, 2H), 3.98 (m, 1H), 3.28 (m, 2H), 3.12 (brs, 4H), 2.81 (brs, 1H), 2.77 (s, 1H), 2.46 (s, 6H), 2.28 (s, 4H), 2.19 (m, 4H), 2.00 (m, 1H), 1.90 (m, 1H), 1.65 (m, 4H).

Example 27A

This example was prepared by substituting pyrrolidine for N-isopropylethylamine in EXAMPLE 4D.

Example 27B

This example was prepared by substituting EXAMPLE 27A for EXAMPLE 4D in EXAMPLE 4E.

Example 27C

This example was prepared by substituting EXAMPLE 27B for EXAMPLE 1D in EXAMPLE 1I.

Example 27D

This example was prepared by substituting EXAMPLE 27C and EXAMPLE 3C for EXAMPLE 1I and EXAMPLE 1M, respectively, in EXAMPLE 1N. $^1$H NMR (400 MHz. DMSO-d$_6$) δ 8.08 (d, 1H), 7.96 (dd, 1H), 7.71 (d, 2H), 7.36 (m, 4H), 7.30 (d, 2H), 7.20 (t, 1H), 7.12 (d, 2H), 6.87 (m, 1H), 6.77 (d, 2H), 6.72 (d, 1H), 4.00 (m, 13.26 (m, 2H), 3.12 (brs, 4H), 2.97 (m, 6H), 2.76 (s, 1H), 2.28 (brs, 4H), 2.19, (m, 4H), 2.05 (m, 1H), 1.95 (m, 1H), 1.82 (brs, 4H), 1.65 (m, 4H).

Example 28

This example was prepared by substituting EXAMPLE 2K and EXAMPLE 17B for EXAMPLE 1M and EXAMPLE 1I, respectively, in EXAMPLE 1N. $^1$H NMR (500 MHz, DMSO-d$_6$) δ 9.59 (brs, 1H), 8.08 (d, 1H), 7.94 (dd, 1H), 7.70 (d, 2H), 7.36 (m, 4H), 7.30 (t, 2H), 7.21 (tt, 1H), 7.09 (d, 2H), 6.83 (d, 1H), 6.78 (d, 3H), 3.97 (m, 1H), 3.28 (m, 2H), 3.13 (brs, 4H), 2.90 (brs, 2H), 2.79 (s, 2H), 2.55 (s, 6H), 2.28 (brs, 4H), 2.20 (m, 2H), 1.99 (s, 2H), 1.90 (m, 2H), 1.42 (t, 2H), 0.96 (s, 6H).

Example 29

This example was prepared by substituting 4-(4-(2-(4-chlorophenyl)cyclo-1-enylmethyl)piperazin-1-yl)benzoic acid, prepared as described in commonly-owned U.S. patent application Ser. No. 10/988,338, and EXAMPLE 27C for EXAMPLE 1M and EXAMPLE 1I, respectively, in EXAMPLE 1N. $^1$H NMR (400 MHz, DMSO-d$_6$) δ 9.60 (brs, 1H), 8.08 (d, 1H), 7.94 (dd, 1H), 7.71 (d, 2H), 7.36 (m, 4H), 7.30 (t, 2H), 7.20 (t, 1H), 7.09 (d, 2H), 6.83 (d, 1H), 6.77 (d, 3H), 3.99 (m, 1H), 3.26 (m, 2H), 3.12 (brs, 4H), 2.80 (m, 5H), 2.76 (s, 2H), 2.40 (m, 4H), 2.3.1 (brs, 4H), 1.99 (m, 1H), 1.89 (m, 1H), 1.77 (brs, 6H), 1.58 (m, 2H), 1.51 (m, 2H).

Example 30A

This example was prepared by substituting EXAMPLE 2E and EXAMPLE 27B for EXAMPLE 1H and EXAMPLE 1D in EXAMPLE 1I.

Example 30B

This example was prepared by substituting EXAMPLE 30A for EXAMPLE 1I and EXAMPLE 1D in EXAMPLE 1N. $^1$H NMR (400 MHz, DMSO-d$_6$) δ 9.57 (brs, 1H), 8.07 (d, 1H), 7.93 (dd, 1H), 7.70 (d, 2H), 7.36 (m, 4H), 7.30 (t, 2H), 7.21 (t, 1H), 7.12 (d, 2H), 6.81 (d, 1H), 6.77 (d, 3H), 3.99 (m, 1H), 3.26 (m, 2H), 3.12 (brs, 4H), 2.80 (m, 5H), 2.76 (s, 2H), 2.27 (m, 4H), 2.22 (m, 2H), 1.99 (m, 3H), 1.88 (m, 1H), 1.77 (brs, 4H), 1.43 (t, 2H), 0.97 (s, 6H).

Example 31

This example was prepared by substituting EXAMPLE 2K and EXAMPLE 30A for EXAMPLE 1M and EXAMPLE 1I, respectively, in EXAMPLE 1N. $^1$H NMR (400 MHz, DMSO-d$_6$) δ 9.52 (brs, 1H), 8.06 (d, 1H), 7.92 (dd, 1H), 7.70 (d, 2H), 7.36 (m, 4H), 7.30 (t, 2H), 7.21 (t, 1H), 7.08 (d, 2H), 6.81 (d, 1H), 6.77 (d, 3H), 3.99 (m, 1H), 3.26 (m, 2H), 3.12 (brs, 4H), 2.76 (s, 2H), 2.75 (m, 5H), 2.26 (m, 4H), 2.20 (m, 2H), 1.99 (m, 3H), 1.86 (m, 1H), 1.76 (brs, 4H), 1.42 (t, 2H), 0.96 (s, 6H).

Example 32

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 30A for EXAMPLE 1M and EXAMPLE 1I, respectively, in EXAMPLE 1N. $^1$H NMR (400 MHz, DMSO-d$_6$) δ 9.50 (brs, 1H), 8.08 (d, 1H), 7.94 (dd, 1H), 7.71 (d, 2H), 7.36 (m, 4H), 7.30 (t, 2H), 7.20 (t, 1H), 7.09 (d, 2H), 6.83 (d, 1H), 6.77 (d, 3H), 3.99 (m, 1H), 3.26 (m, 2H), 3.12 (brs, 4H), 2.80 (m, 5H), 2.76 (s, 2H), 2.40 (m, 4H), 2.31 (brs, 4H), 1.98 (m, 1H), 1.87 (m, 1H), 1.76 (brs, 6H), 1.58 (m, 2H), 1.51 (m, 2H).

Example 33

This example was prepared by substituting EXAMPLE 4F and EXAMPLE 3C for EXAMPLE 1I and EXAMPLE 1M, respectively, in EXAMPLE 1N. $^1$H NMR (300 MHz, DMSO-d$_6$) δ 9.03 (s, 1H), 8.08 (d, 1H), 7.97 (d, 1H), 7.71 (d, 2H), 7.39-7.34 (m, 4H), 7.30 (t, 2H), 7.20 (tt, 1H), 7.13 (dt, 2H), 6.88 (m, 1H), 6.78 (d, 2H), 6.70 (m, 1H), 3.99 (m, 1H), 3.37-3.26 (m, 4H), 3.12 (s, 4H), 2.76 (s, 2H), 2.68-2.53 (m, 2H), 2.34-2.13 (m, 10H), 2.10-1.95 (m, 2H), 1.66 (s, 4H), 1.13 (m, 6H).

Example 34

This example was prepared by substituting EXAMPLE 2K and EXAMPLE 27C for EXAMPLE 1M and EXAMPLE 1I, respectively, in EXAMPLE 1N. $^1$H NMR (300 MHz, DMSO-d$_6$) δ 9.53 (s, 1H), 8.08 (d, 1H), 7.97 (dd, 1H), 7.71 (d, 2H), 7.40-7.34 (m, 4H), 7.30 (t, 2H), 7.20 (tt, 1H), 7.09 (d, 2H), 6.89 (d, 1H), 6.78 (d, 2H), 6.71 (d, 1H), 4.01 (m, 1H), 3.38-3.27 (m, 4H), 3.20-2.84 (m, 10H), 2.79 (s, 2H), 2.27 (s, 4H), 2.20 (t, 2H), 2.03 (m, 2H), 1.85 (m, 4H), 1.42 (t, 2H), 0.96 (s, 6H).

Example 35

This example was prepared by substituting EXAMPLE 3C and EXAMPLE 30A for EXAMPLE 1M and EXAMPLE 1I, respectively in EXAMPLE 1N. $^1$H NMR (400 MHz, DMSO-d6) δ ppm 8.06 (d, 1H), 7.93 (dd, 1H), 7.71 (d, 2H), 7.36 (m, 4H), 7.30 (m, 2H), 7.21 (m, 1H), 7.12 (d, 2H), 6.81 (d, 1H), 6.77 (d, 3H), 3.97 (m, 1H), 3.26 (m, 4H), 3.12 (s, 4H), 2.78 (m, 6H), 2.27 (s, 4H), 2.18 (m, 4H), 1.99 (m, 1H), 1.87 (m, 1H), 1.76 (s, 4H), 1.66 (s, 4H).

Example 36

This example was prepared by substituting EXAMPLE 2K and EXAMPLE 9A for EXAMPLE 1M and EXAMPLE 1I, respectively, in EXAMPLE 1N. $^1$H NMR (400 MHz, DMSO-d$_6$) δ 8.09 (d, 1H), 7.97 (dd, 1H), 7.71 (d, 2H), 7.33 (m, 6H), 7.21 (m, 1H), 7.08 (d, 2H), 6.87 (m, 1H), 6.78 (m, 3H), 3.99 (m, 1H), 3.14 (m, 4H), 2.95 (m, 1H), 2.80 (m, 3H), 2.58 (s, 6H), 2.28 (m, 4H), 2.20 (m, 2H), 1.99 (m, 4H), 1.42 (t, 2H), 0.96 (s, 6H).

Example 37

This example was prepared by substituting EXAMPLE 2K and EXAMPLE 17B for EXAMPLE 1M and EXAMPLE 1I, respectively, in EXAMPLE 1N. $^1$H NMR (400 MHz, DMSO-d$_6$) δ 8.09 (d, 1H), 7.97 (dd, 1H), 7.71 (d, 2H), 7.33 (m, 6H), 7.21 (m, 1H), 7.08 (d, 2H), 6.87 (m, 1H), 6.78 (m, 3H), 3.99 (m, 1H), 3.14 (m, 4H), 2.95 (m, 1H), 2.80 (m, 3H), 2.58 (s, 6H), 2.28 (m, 4H), 2.20 (m, 2H), 1.99 (m, 4H), 1.42 (t, 2H), 0.96 (s, 6H).

Example 38

This example was prepared by substituting 4-(4-(1,1'-biphenyl-2-ylmethyl)-1-piperazinyl)benzoic acid, prepared as described in commonly-owned U.S. patent application Ser. No. 10/988,338, for EXAMPLE 1M and EXAMPLE 17B for EXAMPLE 1I, respectively, in EXAMPLE 1N. $^1$H NMR (400 MHz, DMSO-d$_6$) δ 8.19 (d, 1H), 7.99 (dd, 1H), 7.76 (d, 3H), 7.52 (d, 4H), 7.40 (d, 2H), 7.35 (m, 1H), 7.30 (d, 2H), 7.24 (t, 2H), 7.16 (t, 2H), 6.96 (m, 3H), 4.25 (br, 2H), 4.12 (m, 1H), 3.37 (m, 2H), 3.14 (m, 1H), 3.10 (br, 8H), 2.74 (s, 6H), 2.10 (m, 2H).

Example 39

This example was prepared by substituting 4-(4-(1,1'-biphenyl-2-ylmethyl)-1-piperazinyl)benzoic acid, prepared as described in commonly-owned U.S. patent application Ser. No. 10/988,338, for EXAMPLE 1M in EXAMPLE 1N. $^1$H NMR (400 MHz, DMSO-d$_6$) δ 8.19 (d, 1H), 8.00 (dd, 1H), 7.76 (d, 2H), 7.52 (m, 5H), 7.14 (m, 8H), 6.96 (m, 3H), 4.29 (m, 2H), 4.14 (m, 2H), 4.02 (m, 1H), 3.10 (m, 8H), 2.13 (m, 2H).

The foregoing is meant to illustrate the invention but not to limit it. Variations and changes obvious to one skilled in the art are intended to be within the scope of the invention as defined in the claims.

The invention claimed is:
1. A composition suitable for oral administration comprising an excipient and a compound having formula (II)

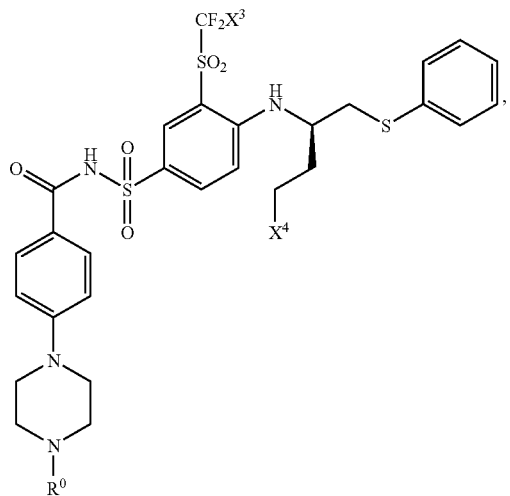

or a therapeutically acceptable salt thereof,
wherein
$X^3$ is Cl or F;
$X^4$ is azepan-1-yl, morpholin-1-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl, and $R^0$ is

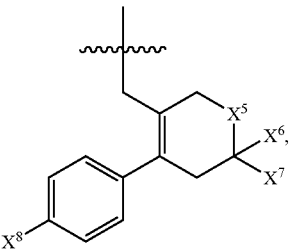

wherein
$X^5$ is $CH_2$, $C(CH_3)_2$ or $CH_2CH_2$;
$X^6$ and $X^7$ are both hydrogen or are both methyl; and
$X^8$ is F, Cl, Br or I.

2. The composition of claim 1, wherein
$X^5$ is $C(CH_3)_2$; and
$X^6$ and $X^7$ are both hydrogen.

3. The composition of claim 1 or claim 2, wherein $X^4$ is morpholin-1-yl.

4. A composition suitable for oral administration comprising an excipient and N-(4-(4-((2-(4-chlorophenyl)-5,5-dimethyl-1-cyclohex-1-en-1-yl)methyl)piperazine-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a therapeutically acceptable salt thereof.

* * * * *

UNITED STATES PATENT AND TRADEMARK OFFICE
CERTIFICATE OF CORRECTION

PATENT NO. : 7,906,505 B2
APPLICATION NO. : 12/772951
DATED : March 15, 2011
INVENTOR(S) : Bruncko et al.

Page 1 of 2

It is certified that error appears in the above-identified patent and that said Letters Patent is hereby corrected as shown below:

Column 2, line 47, replace the "." in "N(CH$_3$)$_2$. N(CH$_3$)(CH(CH$_3$)$_2$)" with a "," to read --N(CH$_3$)$_2$, N(CH$_3$)(CH(CH$_3$)$_2$)--.

Column 6, line 55, replace that portion of the compound name "4,4-d methylcyclohex" with --4,4-dimethylcyclohex--.

Column 13, line 51, replace "hinders" with --binders--.

Column 15, line 47, replace the "." in "PD325901. ARRY-142886," with a "," to read --PD325901, ARRY-142886,--; lines 49-50, replace the "."s in "(CYC-202. R-roscovitine), ZK-304709, PHA-690509. BMI-1040," with ","s to read --(CYC-202, R-roscovitine), ZK-304709, PHA-690509, BMI-1040,--.

Column 18, line 7, replace "TransMiD 107R" with --TransMID 107R--; line 11, replace "Paditaxel" with --paditaxel--.

Column 21, line 1, replace "of to the" with --of the--.

Column 23, Table 3, lines 1-22, delete substituent W$^3$ so that the formula appears as follows:

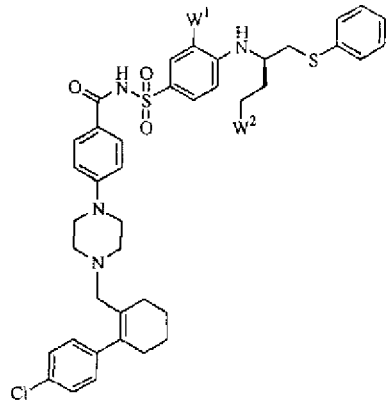

Signed and Sealed this
Eighth Day of November, 2011

David J. Kappos
*Director of the United States Patent and Trademark Office*

CERTIFICATE OF CORRECTION (continued)
U.S. Pat. No. 7,906,505 B2

Column 25, line 2, replace the ":" in "384:" with a ";" to read --384;--.

Column 26, lines 1-2, replace "trifluoroacetyl, triphenylmethyl," with --trifluoroacetyl, trimethylsilyl, triphenylmethyl--; line 46, replace "THE means" with --THF means--.

Column 29, line 60, replace "3.53 (hr, 4H)," with --3.53 (br, 4H),--.

Column 33, line 57, replace the "." in "(300 MHz. DMSO-$d_6$)" with a "," to read --(300 MHz, DMSO-$d_6$)--.

Column 34, lines 41-42, replace the "." in "(300 MHz. DMSO-$d_6$)" with a "," to read --(300 MHz, DMSO-$d_6$)--; line 57, replace "7.94 (d, 17.71 (d, 2H)" with --7.94 (d, 1H), 7.71 (d, 2H)--.

Column 38, line 5, replace "0.97 (s, 61-1)." with --0.97 (s, 6H).--; lines 46-47, replace the "." in "(400 MHz. DMSO-$d_6$)" with a "," to read --(400 MHz, DMSO-$d_6$)--; line 49, replace "4.00 (m, 13.26 (m, 2H)," with --4.00 (m, 1H), 3.26 (m, 2H),--.

Column 39, line 8, replace "2.3.1 (brs, 4H)," with --2.31 (brs, 4H),--.